(12) United States Patent
Kobayashi

(10) Patent No.: US 6,695,819 B2
(45) Date of Patent: Feb. 24, 2004

(54) SAFETY NEEDLE ASSEMBLY

(75) Inventor: Masahiko Kobayashi, Bear, DE (US)

(73) Assignee: Terumo Medical Corporation, Somerset, NJ (US)

( * ) Notice: Subject to any disclaimer, the term of this patent is extended or adjusted under 35 U.S.C. 154(b) by 178 days.

(21) Appl. No.: 09/981,749

(22) Filed: Oct. 19, 2001

(65) Prior Publication Data
US 2003/0078548 A1 Apr. 24, 2003

(51) Int. Cl.⁷ .................................................. A61M 5/32
(52) U.S. Cl. ........................................ 604/192; 604/263
(58) Field of Search .................................. 604/192, 187, 604/263, 110, 198; D24/130; 206/364, 365, 367, 368

(56) References Cited

U.S. PATENT DOCUMENTS

| | | |
|---|---|---|
| 3,658,061 A | 4/1972 | Hall |
| 4,747,836 A | 5/1988 | Luther |
| 4,820,277 A | 4/1989 | Norelli |
| 4,838,871 A | 6/1989 | Luther |
| 4,886,503 A | 12/1989 | Miller |
| 4,909,791 A | 3/1990 | Norelli |
| 4,909,792 A | 3/1990 | Norelli |
| 4,915,696 A | 4/1990 | Feimer |
| 4,944,731 A * | 7/1990 | Cole ........................... 604/192 |
| 4,950,249 A | 8/1990 | Jagger et al. |
| 4,966,591 A * | 10/1990 | Yuen ........................... 604/192 |
| 4,982,842 A | 1/1991 | Hollister |
| 5,011,475 A | 4/1991 | Olson |
| 5,017,189 A | 5/1991 | Boumendil |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,147,319 A * | 9/1992 | Ishikawa et al. ............ 604/174 |
| 5,151,089 A | 9/1992 | Kirk, III et al. |
| 5,152,751 A | 10/1992 | Kozlowski |
| 5,154,285 A | 10/1992 | Hollister |
| 5,188,611 A | 2/1993 | Orgain |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,312,367 A | 5/1994 | Nathan |
| 5,312,369 A | 5/1994 | Arcusin et al. |
| 5,389,083 A | 2/1995 | McCarthy |
| 5,405,332 A | 4/1995 | Opalek |
| 5,445,619 A | 8/1995 | Burns |
| 5,486,163 A | 1/1996 | Haynes |
| 5,490,841 A | 2/1996 | Landis |
| 5,509,907 A | 4/1996 | Bevilacqua |
| 5,584,816 A | 12/1996 | Gyure et al. |
| 5,599,313 A | 2/1997 | Gyure et al. |
| 5,599,318 A | 2/1997 | Sweeney et al. |
| 5,615,771 A * | 4/1997 | Hollister ..................... 206/365 |
| 5,632,732 A | 5/1997 | Szabo et al. |

(List continued on next page.)

Primary Examiner—LoAn H. Thanh
Assistant Examiner—Jennifer Maynard
(74) Attorney, Agent, or Firm—Burns, Doane, Swecker & Mathis, LLP

(57) ABSTRACT

A safety needle assembly includes a cannula connected to a hub, and a protector positioned over and covering the cannula. The protector is provided with an opening and is axially movable between a covering position and an uncovering position. A sheath provided with a channel is pivotally mounted with respect to the hub and is positioned in an initial position in which the through opening in the protector is closed by the sheath. The sheath is adapted to be pivoted away from the cannula towards an intermediate position and is adapted to be pivoted back towards the cannula to a cannula covering position in which the cannula is located within the channel. An engaging part of the protector engages the sheath during movement of the protector from the covering position to the uncovering position to cause the sheath to automatically pivot away from the initial position.

45 Claims, 13 Drawing Sheets

U.S. PATENT DOCUMENTS

| | | |
|---|---|---|
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,672,161 A | 9/1997 | Allen et al. |
| 5,693,022 A | 12/1997 | Haynes |
| 5,704,920 A | 1/1998 | Gyure |
| 5,733,265 A | 3/1998 | Bachman et al. |
| 5,735,827 A * | 4/1998 | Adwers et al. ............. 604/263 |
| 5,738,665 A | 4/1998 | Caizza et al. |
| 5,746,726 A | 5/1998 | Sweeney et al. |
| 5,807,351 A | 9/1998 | Kashmer |
| 5,814,018 A * | 9/1998 | Elson et al. ................. 604/110 |
| 5,836,920 A | 11/1998 | Robertson |
| 5,868,716 A | 2/1999 | Sweeney et al. |
| 5,891,103 A | 4/1999 | Burns |
| 5,910,130 A | 6/1999 | Caizza et al. |
| 5,913,846 A | 6/1999 | Szabo |
| 5,919,165 A | 7/1999 | Benson |
| 5,925,032 A | 7/1999 | Clements |
| 5,993,426 A | 11/1999 | Hollister |
| 6,120,482 A * | 9/2000 | Szabo ........................ 604/192 |
| 6,156,012 A * | 12/2000 | Nathan ....................... 604/192 |
| 6,413,243 B1 * | 7/2002 | Geist .......................... 604/192 |

\* cited by examiner

SAFETY NEEDLE ASSEMBLY

FIELD OF THE INVENTION

The present invention generally relates to needle assemblies. More particularly, the present invention pertains to a safety mechanism for use in connection with needle assemblies including hypodermic needles, catheter needles and other medical instruments.

BACKGROUND OF THE INVENTION

Needle assemblies used in medical procedures have been and continue to be a concern from the standpoint of healthcare worker safety. Accidental needlesticks with a used needle present the possibility for transmission of disease. The most basic form of needlestick prevention involves the use of a rigid cylindrical cap. The rigid cylindrical cap is positioned over the cannula and engages the hub to which the cannula is connected. During use, the cylindrical cap is removed to expose the cannula. After using the syringe/needle assembly for its intended procedure, the cylindrical cap must be once again mounted on the hub to cover the used cannula. Oftentimes, the healthcare professional tries to reposition the cylindrical cap on the syringe/needle assembly by "scooping" the cylindrical cap with the syringe/needle assembly. As can be appreciated, this may not be an easy or effective technique for repositioning the protective cap on the syringe/needle assembly. Also, the cap may become accidentally dislodged from the syringe/needle assembly, thus exposing the used cannula and presenting a potential danger.

Other proposals have also been made to protect healthcare professionals from needle stick hazards. These proposals are generally divided into three categories: 1) hinged recap devices in which a hinged sleeve is pivoted into a permanently locked position with respect to the cannula; 2) spring-loaded retractable cannula devices in which a spring-connected cannula is activated and the cannula in turn is retracted into the syringe barrel or the syringe plunger; and 3) sliding barrel devices in which the syringe barrel is formed by two concentric cylinders, the outer one of which is slid by the health care worker towards the cannula after use to cover the cannula. Although these assemblies provide some measure of protection against accidental needlesticks, difficulties remain.

For example, hinged recap devices are assembled between the syringe and needle assembly. This construction introduces dead space between the cannula and the syringe, thereby resulting in the waste of expensive medication. Retractable cannula devices run the risk of inadvertently retracting, thus wasting a syringe and once again presenting the possibility of wasting expensive medication. Additionally, the velocity of the cannula retraction could result in the spraying or splashing of fluids or medication, thus actually increasing the healthcare professional's exposure risk. The sliding barrel design is disadvantageous in that it almost doubles the length of the syringe from the unused position to the used/disabled/engaged position, thus substantially increasing the volume of biohazard waste and possibly creating exposure hazards because the syringe/needle assembly does not adequately fit into the sharps container.

Another disadvantage associated with these alternative designs involves the manufacturing and assembly cost. To make the manufacture of a safety needle or safety syringe cost effective, automated manufacturing equipment must be utilized. However, by virtue of their construction, the syringe/needle assemblies discussed above cannot be manufactured using the same automated equipment that is currently used for producing needle assemblies in which the cannula is simply covered by a cylindrical cap.

The automated manufacture of the needle assemblies mentioned above in which a cylindrical cap covers the needle typically involves fixing the cannula to the hub and then mounting the cylindrical cap on the hub so that the cap covers the cannula. The resulting covered needle assembly can then be packaged and sold as a separate assembly for attachment to and use in connection with any desired syringe. Alternatively, the resulting covered needle assembly can be connected to a syringe to produce a syringe/needle assembly that is then packaged and sold. In the latter case, automated equipment is used to connect the covered needle assembly to the syringe. This automated equipment is designed to handle or accommodate the cylindrical rigid cap that is mounted on the needle assembly for purposes of connecting the covered needle assembly to the syringe. The various types of alternative safety mechanisms mentioned above possess a configuration that is different from the known covered needle assemblies that involve the use of a rigid cylindrical cap. Thus, this automated equipment is unable to handle or accommodate these alternative safety mechanisms and cannot be used to connect these alternative safety mechanisms to a syringe.

In light of the foregoing, a need exists for a safety needle assembly that is constructed to provide the desired protection against accidental needle sticks while at the same time being capable of being handled in an automated manner, preferably through use of existing machinery.

SUMMARY OF THE INVENTION

According to one aspect of the invention, a safety needle assembly includes a hub having a proximal end adapted to be connected to a fluid transfer device and a distal end, a cannula having a proximal end connected to the hub and a distal end, a collar mounted on the hub, and a protector provided with a through opening. The protector is movable between an initial position in which the cannula is at least partially covered by the protector and a removed position in which the cannula is uncovered by the protector. A sheath is pivotally mounted on the collar and is positioned in an initial position in which the through opening in the protector is closed by the sheath. The sheath includes a longitudinally extending channel and is adapted to pivot from the initial position in a direction away from the cannula to permit use of the cannula and is adapted to pivot back towards the cannula to a cannula covering position in which the cannula is located within the channel of the sheath. The protector is provided with an engaging part that engages the sheath during movement of the protector from the covering position to the removed position to cause the sheath to automatically pivot away from the initial position. The safety needle assembly is also provided with a mechanism for permanently locking the sheath in the cannula covering position.

According to another aspect of the invention, a safety needle assembly includes a hub having a proximal end adapted to be connected to a fluid transfer device and a distal end, a cannula having a proximal end connected to the hub and a distal end, and a protector having an interior and an opening that communicates with the interior of the protector. The protector is positioned in an initial position in which the protector at least partially covers the cannula and is adapted to be removed so that the cannula is uncovered by the protector. A sheath is pivotally mounted with respect to the hub and is configured to define a channel. At least one cannula engaging projection is provided on the sheath and extends into the channel. The sheath is positioned in an initial position in which at least a portion of the sheath extends through the opening in the protector and into the interior of the protector. The sheath is adapted to pivot away from the cannula and out through the opening in the protector and is adapted, after the protector is removed, to pivot back towards the cannula to a cannula locking position in which the cannula is lockingly engaged by the at least one cannula engaging projection. The assembly also includes a mechanism for preventing the cannula engaging projection from lockingly engaging the cannula when the sheath is in the initial position.

According a further aspect of the invention, a safety needle assembly includes a hub having a proximal end adapted to be connected to a fluid transfer device and a distal end, a cannula having a proximal end connected to the hub and a distal end, a collar mounted on the hub, and a protector mounted on the collar and provided with a through opening. The protector is movable from an initial position in which the protector at least partially surrounds the cannula to a removed condition in which the cannula is uncovered by the protector. A sheath is pivotally mounted on the collar and is positioned in an initial position in which the through opening in the protector is closed by the sheath. The sheath includes a longitudinally extending channel and is adapted to be pivoted from the initial position in a direction away from the cannula and to be pivoted in a direction back towards the cannula to a cannula covering position in which the cannula is located within the channel of the sheath. The safety needle assembly also includes a mechanism for locking the sheath in the cannula covering position. The collar has at least one surface portion which is engaged by a portion of the sheath when the sheath is in the initial position to produce a first frictional engaging force between the collar and the hub sufficient to cause the collar and the hub to rotate together as a unit and which is disengaged from the portion of the sheath when the sheath is pivoted away from the initial position to reduce the frictional engaging force between the collar and the hub to permit the collar to rotate relative to the hub.

In accordance with another aspect of the invention, a safety needle assembly includes a hub having a proximal end adapted to be connected to a fluid transfer device and a distal end, a cannula having a proximal end connected to the hub and a distal end, a collar mounted on the hub, and a protector mounted on the collar and provided with a through opening. The protector is mounted on the collar in an initial position in which the protector at least partially covers the cannula and is movable to separate the protector from the collar so that the cannula is uncovered by the protector. A sheath is pivotally mounted on the collar and is positioned in an initial position in which the through opening in the protector is closed by the sheath. The sheath includes a longitudinally extending channel and is adapted to pivot from the initial position in a direction away from the cannula and is adapted to pivot back towards the cannula to a cannula covering position in which the cannula is located within the channel of the sheath. The protector and the sheath each have an outer surface configured as a part of a cylinder, with the protector and the sheath together defining a cylindrical outer surface when the protector is in the initial position and the sheath is in the initial position.

In accordance with another aspect of the invention, a safety needle assembly includes a hub having a proximal end adapted to be connected to a fluid transfer device and a distal end, a cannula having a proximal end connected to the hub and a distal end, a collar mounted on the hub, and a protector having a wall in which is provided an opening. The protector is positioned in an initial position in which the protector covers at least a portion of the cannula and is movable from the initial position to a removed position in which the cannula is uncovered by the protector. A sheath is pivotally mounted on the collar in an initial position in which at least a portion of the sheath extends through the opening in the wall of the protector. The sheath includes side walls and a back wall defining a channel. The sheath is adapted to be pivoted away from the cannula and out through the opening in the wall of the protector and is adapted to be pivoted back towards the cannula to a cannula covering position in which the cannula is positioned within the channel once the protector has been moved to the removed position. A mechanism is also provided for preventing the sheath in the initial position from freely pivoting out of the opening in the wall of the protector in the absence of a force causing pivoting movement of the sheath.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements and wherein.

DETAILED DESCRIPTION OF THE INVENTION

Figure 1:
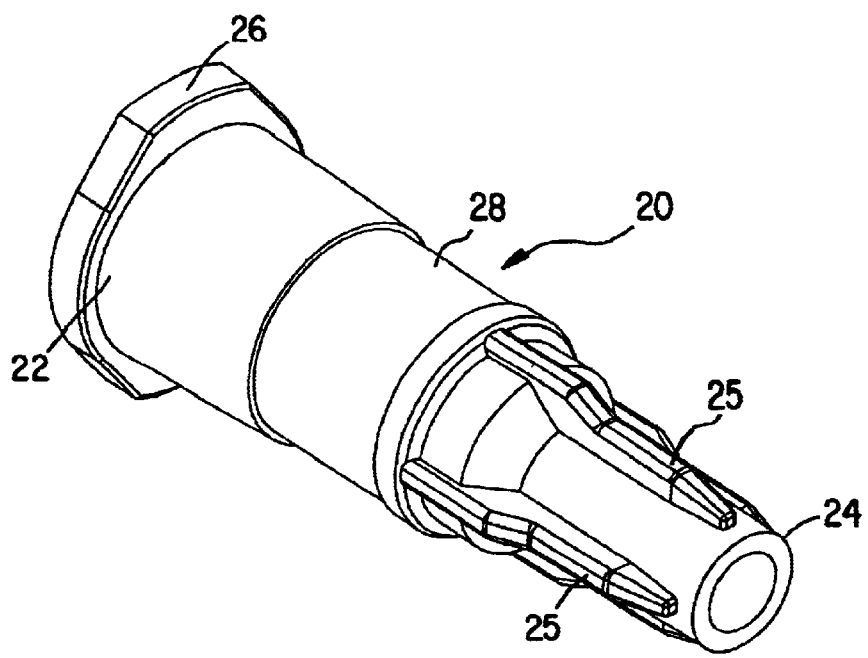
FIG. 1 is a perspective view of the hub used in the safety needle assembly of the present invention.

Referring initially to FIGS. 1–4, the safety needle assembly of the present invention includes a hub 20, a collar 30, a protector 50 and a sheath 70. As illustrated in FIG. 1, the hub 20 includes a proximal end 22 and a distal end 24. A lumen extends along the entire hub 20 and is open at both the proximal end 22 as well as the distal end 24. Although not specifically illustrated in FIG. 1, the distal end 24 of the hub 20 is adapted to receive a cannula which is fixed in place relative to the hub 20. The cannula also possesses a lumen and the lumen in the cannula communicates with the lumen in the hub 20. The proximal end 22 of the hub 20 is provided with a ridge 26 that is adapted to mate with a fluid transfer device, such as the distal end of a syringe barrel, using a known luer lock fitting. The hub 20 is also provided with a recessed region 28 at a location intermediate the distal end 24 and the proximal end 22 of the hub 20.

Figure 2:
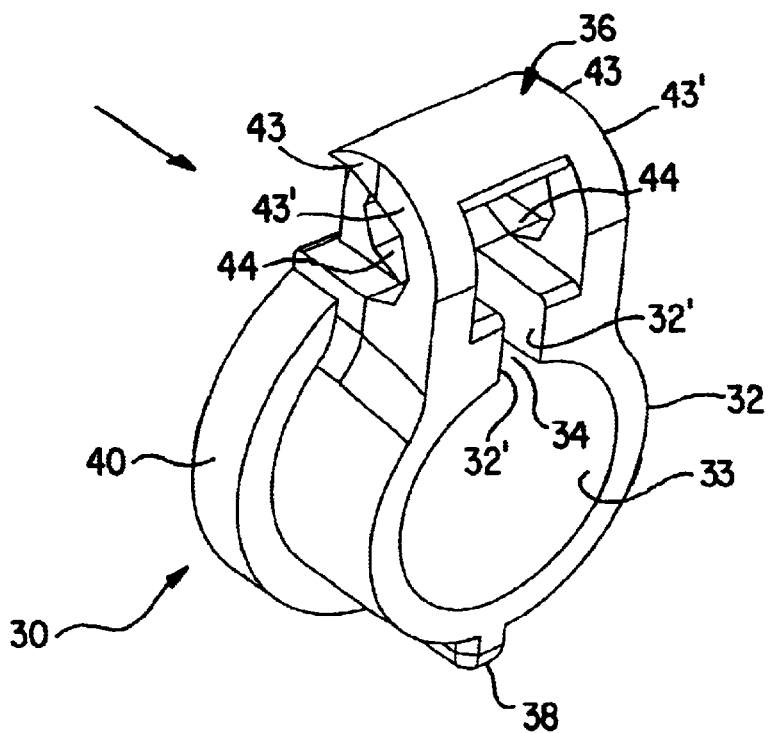
FIG. 2 is a perspective view of the collar used in the safety needle assembly of the present invention.

Referring to FIG. 2, the collar 30 includes a generally annular or ring shaped portion 32, which defines a centrally located hole 33, and an upstanding rib portion 36. The rib member 36 is provided with a pair of laterally extending through holes 44, 44. The annular portion 32 is provided with a split 34 in the region of the radially outwardly directed rib 36 so that the rib 36 spans and extends across the split 34. The split 34 defines circumferentially spaced apart ends 32', 32' of the annular portion 32.

The collar 30 is also provided with a second radially outwardly directed rib portion 38. In the illustrated embodiment of the collar 30, the second rib portion 38 is positioned diametrically opposite the first rib portion 36. As can be seen from the illustration in FIG. 2, the first rib portion 36 possesses a greater width than the second rib portion 38.

The collar 30 also includes a radially outwardly directed ridge 40 at one axial end of the collar 30. This ridge 40 extends circumferentially around at least a portion of the outer circumference of the collar 30.

Figure 7:
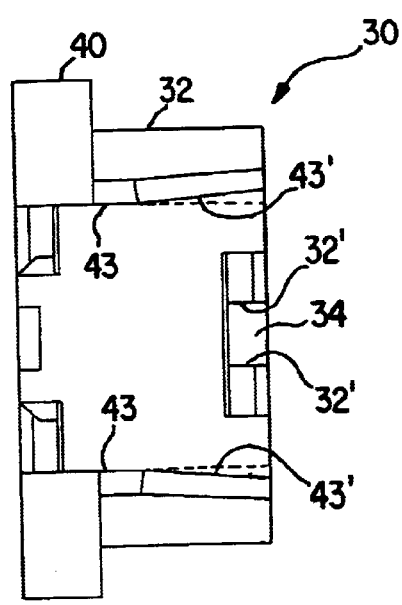
FIG. 7 is a top view of the collar shown in FIG. 2.

The first rib portion 36 possesses a pair of laterally outwardly facing side surfaces 43, 43. As illustrated in FIG. 7 which is a top view of the collar 30, at least a portion 43', 43' of the side surfaces 43, 43 of the first rib portion 36 are nonparallel to one another. That is, a portion 43', 43' of the side surfaces 43, 43 are slightly inclined outwardly away from one another in a direction away from the ridge 40. In the illustrated embodiment, the outward inclination of the side surface portions 43', 43' begins at a point on the rib portion 36 located forwardly of the ridge 40. The purpose for the inclined side surface portions 43', 43' on the rib portion 36 of the collar 30 will become more apparent from the discussion below. The outward angle of inclination of the side surface portions 43', 43' can be on the order of approximately 5° (i.e., the angle between each side surface portion 43' and the dotted line shown in FIG. 7 is approximately 5°), although other values can be employed.

Figure 3:
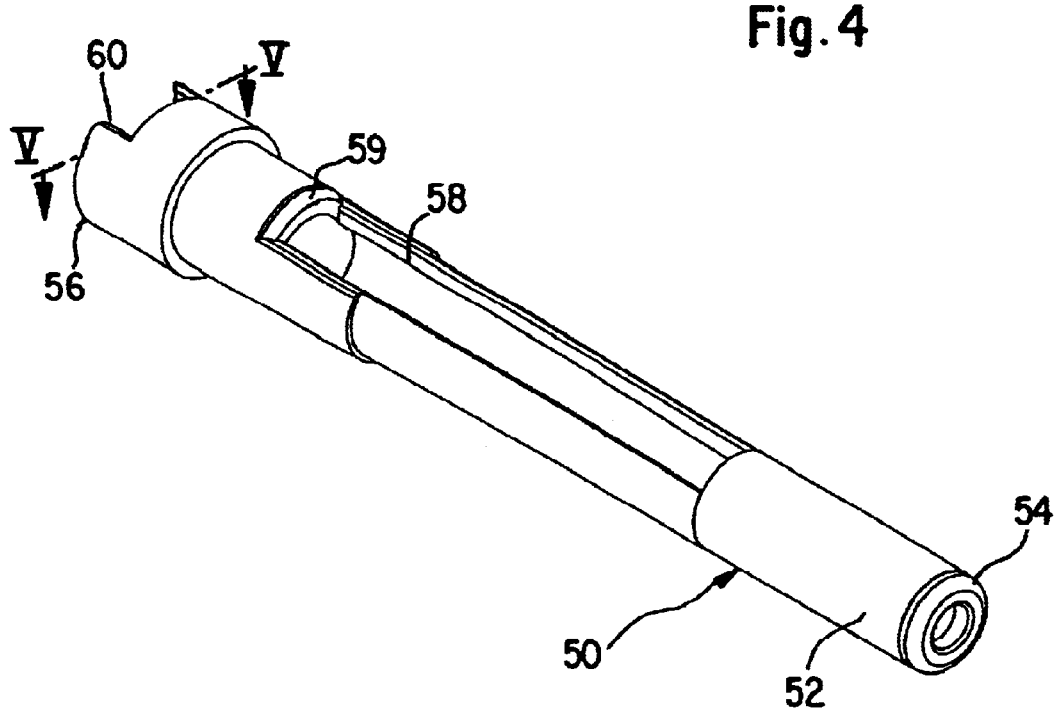
FIG. 3 is a perspective view of the protector used in the safety needle assembly of the present invention.

As illustrated in FIG. 3, the protector 50 is in the form of an elongated generally cylindrical member 52 possessing a distal end 54 and a proximal end 56. In the illustrated version of the protector 50 shown in FIG. 3, the proximal end portion of the protector 50 possesses a slightly enlarged diameter. Both the distal end 54 of the protector 50 and the proximal end 56 of the protector 50 are open, although the distal end 54 of the protector 50 could be closed. The protector 50 is provided with a longitudinally extending slot or opening 58 that opens to the interior of the cylindrical member 52. The slot or opening 58 extends generally parallel to the axis of the cylindrical member 52.

Figure 5:
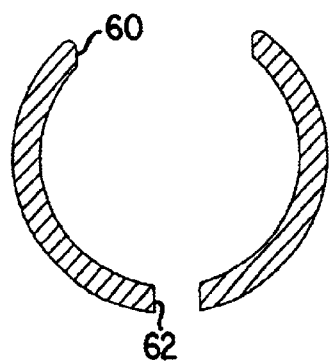
FIG. 5 is a cross-sectional view of the protector taken along the section line V—V in FIG. 3.

FIG. 5 illustrates the configuration of the proximal end 56 of the protector 50. Here, the sheath 70 is provided with two cutouts 60, 62 which, in the illustrated embodiment, are positioned diametrically opposite one another. One of the cutouts 60, constituting a first cutout, is larger in size (i.e., has a greater circumferential extent or width) than the other cutout 62, which constitutes a second cutout. As seen in FIG. 3, the first cutout 60 is circumferentially aligned with the opening 58 in the protector 50.

Figure 4:
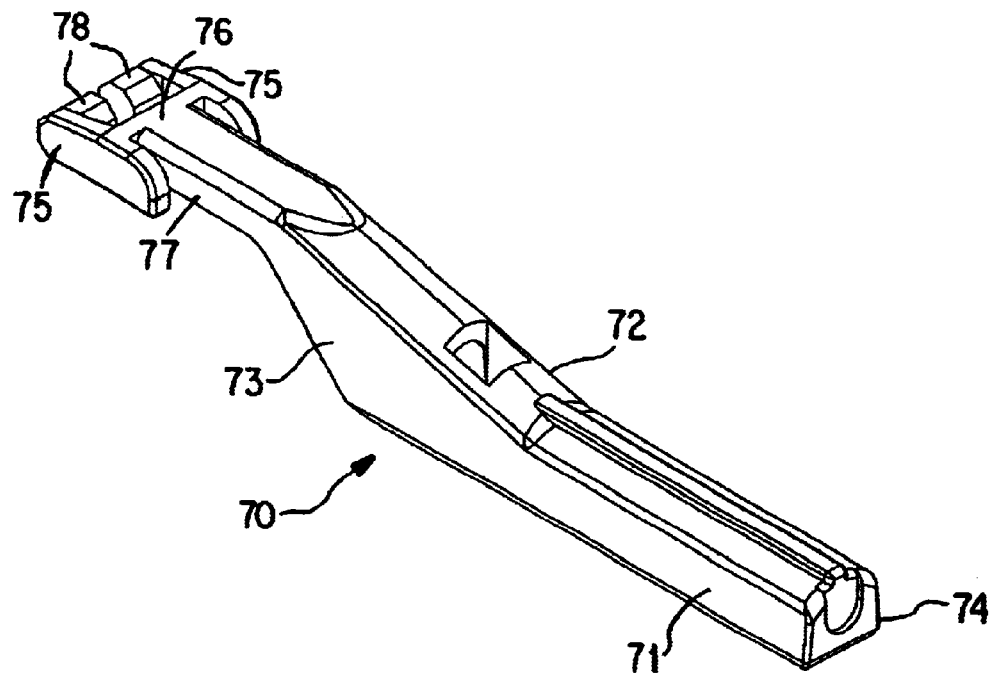
FIG. 4 is a perspective view of the sheath used in the safety needle assembly of the present invention.

As seen in FIG. 4, the sheath 70 is in the form of a generally elongated member 72 possessing a distal end 74 and a proximal end 76. The distal end 74 of the sheath 70 is closed as seen in FIG. 4. The proximal end 76 of the sheath 70 is provided with two spaced apart arms 75, 75. Each of the arms 75, 75 is provided with an inwardly extending lug 78, 78. The two lugs 78, 78 are positioned in axial alignment and opposing relation to one another.

The sheath 70 is comprised of a cannula covering portion 71, a collar connecting portion 77 and an intermediate portion 73 which forms a protector engaging portion. As can be seen from FIG. 4, the cannula covering portion 71 and the collar connecting portion 77 are generally parallel to one another, but offset from each other (i.e., the axis of the cannula covering portion 71 and the axis of the collar connecting portion 77 are offset or spaced from one another). The intermediate portion 73 is inclined and extends between the cannula covering portion 71 and the collar connecting portion 77.

Figure 6:
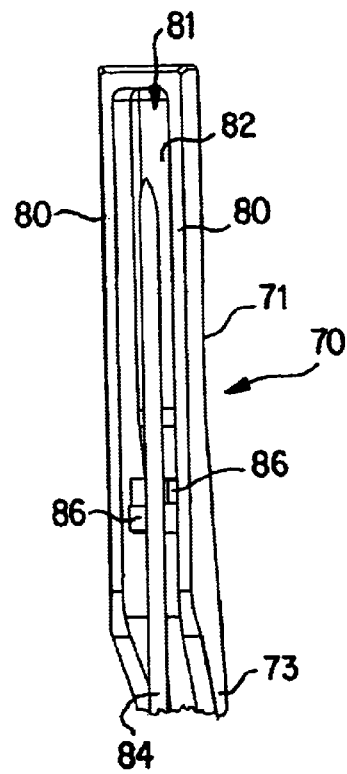
FIG. 6 is a perspective view of the interior of the sheath shown in FIG. 4.

As seen more clearly in FIG. 6, the cannula covering portion 71 of the sheath 70 is configured to define a longitudinally extending channel 81. The longitudinally extending channel 81 is defined by two oppositely positioned side walls 80, 80 connected to one another by a back wall 82. The longitudinally extending channel 81 defined by the side walls 80, 80 and the back wall 82 is designed to receive the cannula 84 which is generally illustrated in FIG. 6. Extending inwardly from each of the side walls 80, 80 of the sheath 70, or possibly the back wall 82 of the sheath, are several cannula retaining devices 86, 86 which may be in the form of cannula engaging projections or barbs that are designed to capture and permanently retain the cannula within the channel 81 once the cannula is received within the channel to a sufficient extent.

Generally speaking, one way of assembling the safety needle assembly involves fixing a cannula to the distal end 24 of the hub 20, mounting the protector 50 on the collar 30, and connecting the sheath 70 to the collar 30. With respect to the connection of the cannula to the distal end of the hub 20, this can be accomplished in the typical way using known techniques.

Mounting the protector 50 on the collar 30 involves orienting the protector 50 relative to the collar 30 such that the larger cutout 60 is aligned with and able to receive the larger rib 36 while the smaller cutout 62 is aligned with and able to receive the smaller rib 38. Thus, the different sized ribs 36, 38 on the collar 30 and the different sized cutouts 60, 62 on the protector 50 provide a mechanism for ensuring that the protector 50 can only be positioned in one rotational position or orientation relative to the collar 30. With the cutouts 60, 62 aligned with the ribs 36, 38, the protector 50 can be slid over the collar 30 until the protector 50 contacts the ridge 40 at the proximal end of the collar 30.

The collar 30, with the protector 50 mounted on the collar 30, is adapted to be mounted in the recessed region 28 of the hub 20 (with the connected cannula). This mounting of the collar 30 on the recessed region 28 of the hub 20 can be accomplished by axially sliding the collar 30 from the distal end 24 of the hub 20 towards the proximal end 22 of the hub 20 until the collar 30 is received on the recessed region 28 of the hub 20. In this way, the collar 30 is mounted on the hub 20, with the protector 50 covering the cannula. As described below in more detail, the collar 30 is mounted on the hub 20 so that the collar 30 is capable of rotating on the hub 20 depending upon the position of the sheath 70 relative to the collar 30.

To mount the sheath 70 on the collar 30, the proximal end 76 of the sheath 70 is positioned in facing relation to the side of the collar 30 adjacent the ridge 40 so that the lugs 78, 78 are positioned close to the holes 44, 44 in the rib portion 36. The sheath 70 is then pushed towards the collar 30 in the direction of the arrow shown in FIG. 2 (or the collar 30 is pushed towards the sheath 70 in the opposite direction, or the collar 30 and sheath 70 are pushed towards one another) to cause the arms 75, 75 on the sheath 70 to spread apart so that the lugs 78, 78 on the arms 75, 75 can be received in the holes 44, 44 in the rib portion 36 of the collar 30. Once the lugs 78, 78 are positioned in the respective holes 44, 44, the sheath 70 is mounted on the collar in a manner that allows the sheath 70 to pivot or rotate about the common axis of the lugs 78, 78.

Figure 8:
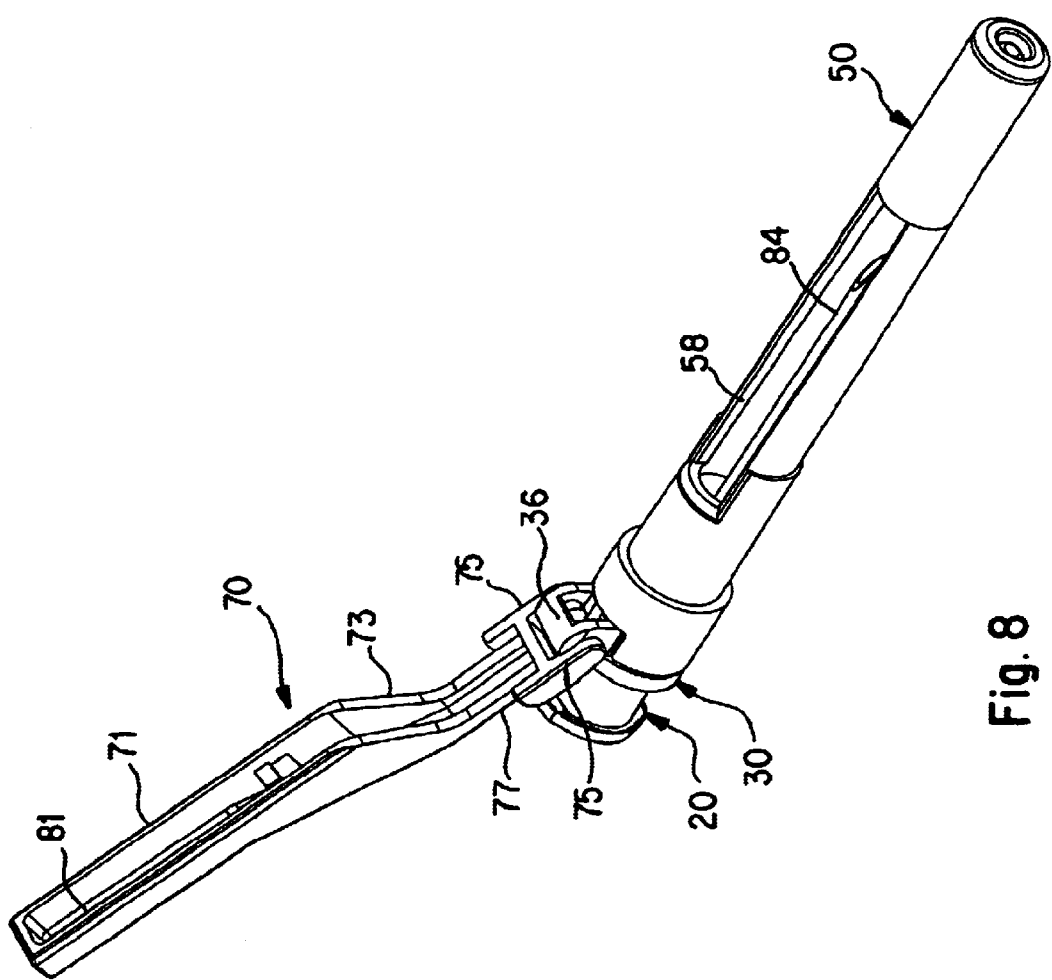
FIG. 8 is a perspective view of the safety needle assembly of the present invention with the sheath positioned prior to pivoting towards the protector.
Figure 9:
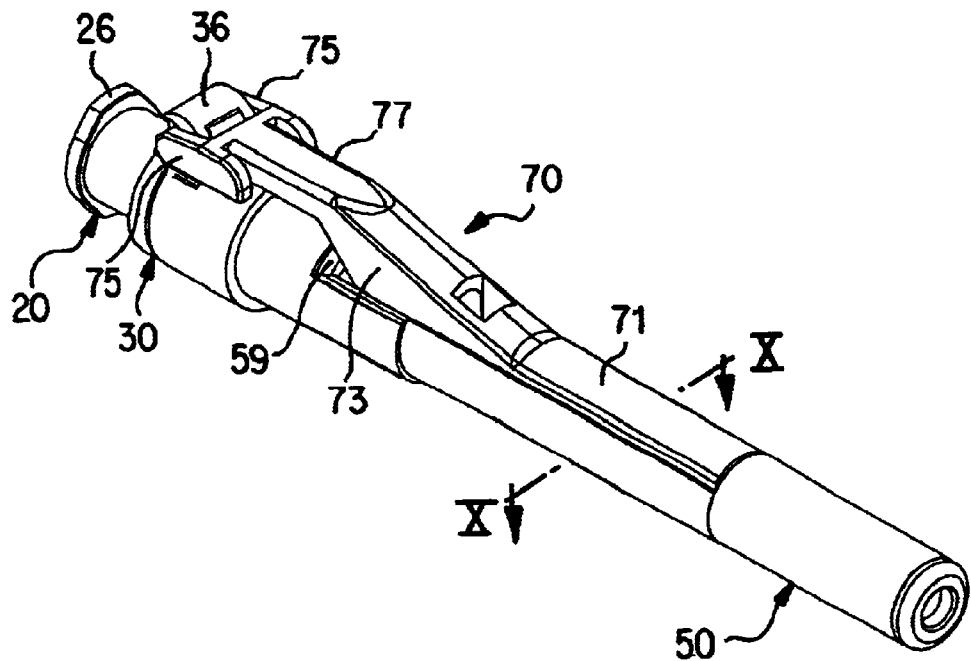
FIG. 9 is a perspective view of the safety needle assembly shown in FIG. 8 in the assembled condition.
Figure 10:
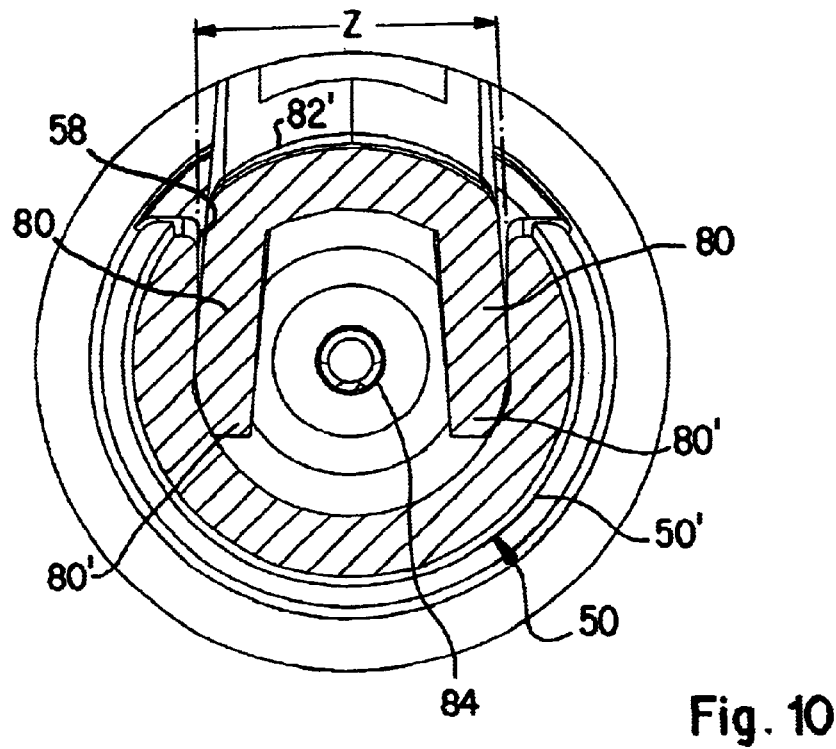
FIG. 10 is a cross-sectional view of a portion of the safety needle assembly in the assembled condition taken along the section line X—X in FIG. 9.

FIG. 8 illustrates the safety needle assembly after the collar 30 and protector 50 have been mounted on the hub 20, and the sheath 70 has been connected to the collar 30. From this condition, the sheath 70 must be pivoted into the position shown in FIG. 9 which illustrates the safety needle assembly in the assembled condition. The length of the cannula covering portion 71 of the sheath 70 shown in FIG. 4 is generally approximately equal to the length or longitudinal extent of the opening 58 in the protector 50. As the sheath 70 is pivoted towards the protector 50 from the position shown in FIG. 8, the sheath 70 is pivoted relative to the collar 30 and the protector 50 so that the cannula covering portion 71 of the sheath 70 enters into the opening 58 in the protector 50. The side walls 80, 80 of the sheath 70 thus extend into the interior of the protector 50 as shown in FIGS. 9 and 10. Thus, the sheath 70 closes or covers the opening 58 in the protector 50.

The opening 58 in the protector 50 and the sheath 70 are designed so that when the sheath 70 is pivoted to the position shown in FIG. 9, the sheath 70 is inhibited from freely pivoting in the opposite direction toward the position illustrated in FIG. 8. That is, as described in more detail, the sheath 70 can be pivoted from the position shown in FIG. 9 towards the position shown in FIG. 8 upon application of a force to the sheath 70, but the sheath 70 is inhibited from freely pivoting towards the position shown in FIG. 8 in the absence of such a force applied to the sheath 70.

Figure 11:
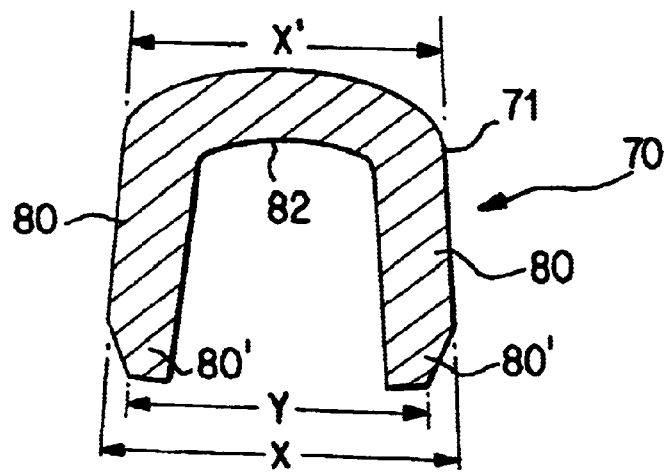
FIG. 11 is a an enlarged cross-sectional view of the sheath.

As shown in FIG. 11, the side walls 80, 80 of the cannula covering portion 71 of the sheath 70 diverge or expand outwardly away from one another towards the free ends of the side walls 80, 80 so that the dimension X between the side walls 80, 80 adjacent the free ends of the side walls is greater than the distance X' between the side walls 80, 80 adjacent the back wall 82. In addition, as further seen in FIG. 11, each of the side walls 80, 80 has a tapered tip portion 80', 80' dimensioned so that the distance Y between the tapered tip portions 80', 80' at the free ends of the side walls 80, 80 is less than the dimension X.

Further, as seen with reference to FIG. 10, the dimension Z representing the width of the opening 58 in the protector 50 is less than the dimension X and is slightly greater than the dimension Y. With this construction, as the sheath 70 is pivoted from the position shown in FIG. 8 towards the position shown in FIG. 9, the tapered tip portions 80', 80' of the sheath side walls 80, 80 are able to enter the opening 58 in the protector 50, with the tapered tip portions facilitating entry of the side walls into the interior of the protector 50. The protector is made of a material (e.g., plastic) which allows the side walls 80, 80 to slightly flex inwardly as the side walls 80, 80 enter farther into the protector 50. With the sheath 70 in the position shown in FIGS. 9 and 10, the side walls 80, 80 of the sheath 70 tend to push outwardly against a portion of the inner surface of the protector 50, thus inhibiting the sheath 70 from freely pivoting out of the opening 58 of the protector 50. This thus provides a mechanism for retaining the sheath 70 in the assembled condition shown in FIGS. 9 and 10 (or inhibiting the sheath 70 from pivoting away from the assembled condition) until a force is applied to the sheath 70 to overcome the engaging force described above.

When the safety needle assembly is in the assembled condition shown in FIG. 9 so that the sheath 70 covers the opening 58 in the protector 50 (i.e., the sheath 70 is positioned in the opening 58 in the protector 50), it is important that the cannula retaining devices 86, 86 shown in FIG. 6 be incapable of lockingly engaging the cannula 84 to prevent the sheath 70 from being locked in the cannula covering position. For this reason, the safety needle assembly is provided with a mechanism for preventing the cannula retaining devices 86, 86 from lockingly engaging the cannula 84 when the sheath 70 and the protector 50 are in their initial positions shown in FIGS. 9 and 10 (i.e., when the safety needle assembly is in the assembled condition). In this embodiment, the sheath 70 and the protector 50 are dimensioned and configured so that when the sheath 70 is in the initial position, the tip ends 80', 80' of the sheath 70 contact the inner surface of the protector 50 and prevent the sheath 70 from being pivoted to a position which would cause the cannula retaining devices 86, 86 to lockingly engage and lockingly retain the cannula 84.

As can be seen from FIGS. 9 and 10, when the sheath 70 has been pivoted to the assembled condition illustrated in FIGS. 9 and 10 so that the sheath 70 and the protector 50 are in their initial positions, the sheath 70 forms a part of the cylindrical shape of the protector 50. In this regard, the outer surface 82' of the back wall 82 of the cannula covering portion 71 of the sheath 70 is curved. The curvature (i.e., radius of curvature) of the outer surface 82' of the back wall 82 of the cannula covering portion 71 of the sheath 70 substantially matches or is substantially the same as the curvature (i.e., radius of curvature) of the outer surface 50' of the protector 50. Further, the sheath 70 and the protector 50 are dimensioned so that when the sheath 70 is positioned within the opening 58 in the protector 50 in the initial position shown in FIGS. 9 and 10, the circumferential curvature of the outer surface 82' of the back wall 82 of the cannula covering portion 71 of the sheath 70 generally matches the circumferential curvature of the outer surface of the protector 50. The outward appearance of the safety needle assembly thus resembles that of the rigid cylindrical caps which have been used in the past to cover and protect needles. That is, because the safety needle assembly of the present invention is designed so that the cannula covering portion 71 of the sheath 70 forms a part of the cylindrical shape of the protector 50, the safety needle assembly of the present invention has an appearance which, to automated equipment, is little different from the appearance of currently used needle assemblies in which a rigid cylindrical cap is mounted on a hub and covers the cannula. This is advantageous from a manufacturing standpoint in that the automated machinery that is used to handle and connect known types of covered needle assemblies (i.e., needle assemblies in which a rigid cylindrical cap is mounted on the hub) to a syringe can also be used with the safety needle assembly of the present invention. Thus, the safety needle assembly of the present invention can be handled and connected to a syringe in an automated fashion without the need for new automated equipment or a significant redesign of existing automated equipment.

During the pivoting movement of the sheath to the initial position shown in FIG. 9, the inner surfaces of the arms 75, 75 of the sheath 70 (i.e., the surfaces of the arms 75, 75 from which the lugs 78, 78 extend) engage the inclined outer surface portions 43', 43' of the rib portion 36 of the collar 30. As described above, the inclined outer surface portions 43', 43' of the rib portion 36 are slightly inclined outwardly in the direction away from the ridge 40 (i.e., in the direction towards the distal end of the protector 50). As the arms 75, 75 engage the inclined outer surface portions 43', 43' of the rib portion 36 during the pivoting movement of the sheath 70 towards the initial position shown in FIG. 9, the circumferentially spaced apart ends 32', 32' of the annular portion 32 are urged towards one another. Thus, the size of the hole 33 in the collar 30 is reduced and so the frictional engagement force between the collar 30 and the hub 20 is increased or tightened. When the sheath 70 reaches the initial position shown in FIG. 9 (i.e., the assembled condition of the safety needle assembly), the frictional engagement force between the collar 30 and the hub 20 is sufficiently great to prevent the collar 30 from rotating on the hub 20.

It is to be noted that when the sheath 70 is in the position shown in FIG. 8, the collar 30 is capable of rotating relative to the hub 20. The inner diameter of the hole 33 in the collar 30 is dimensioned relative to the outer diameter of the recessed region 28 on the hub 20 so that when the sheath 70 is positioned relative to the collar 30 in the manner shown in FIG. 8, a force applied to the sheath 70 allows the collar 30 to rotate on the hub 20. Preferably, the inner diameter of the hole 33 in the collar 30 and the outer diameter of the recessed region 28 on the hub 20 are dimensioned so that a frictional force exists between the collar 30 and the hub 20 which is sufficient to prevent free rotation of the collar 30 on the hub 20 when the sheath 70 is positioned in the manner shown in FIG. 8. Thus, in the position shown in FIG. 8, the collar 30 is preferably not able to freely rotate on the hub 20 (i.e., is not able to rotate in the absence of a rotational force applied to the collar), but is capable of rotating on the hub 20 when a rotational force is applied to the collar 30 by way of the sheath 70. However, as the sheath 70 is pivoted towards the initial position shown in FIG. 9, the circumferentially spaced apart ends 32', 32' of the annular portion 32 of the collar move towards each other and increase the frictional engagement between the outer surface of the recessed portion 28 of the hub 20 and the inner surface of the hole 33 in the collar 30. Once the sheath 70 reaches the initial position shown in FIG. 9, the frictional engagement force between the outer surface of the recessed portion 28 of the hub 20 and the inner surface of the hole 33 in the collar 30 is sufficient to prevent relative rotation between the collar 30 and the hub 20. Thus, the outwardly inclined outer surface portions 43', 43' on the rib portion 36 of the collar 30, in cooperation with the arms 75, 75 of the sheath, provide a mechanism for varying the frictional engaging force between the collar 30 and the hub 20 depending upon the position of the sheath 70. In the assembled condition of the safety needle assembly shown in FIG. 9 in which the sheath 70 is located in the illustrated initial position, the frictional engaging force between the collar 30 and the hub 20 prevents the collar 30 from rotating on the hub 20. On the other hand, this frictional engaging force is reduced as the sheath 70 is pivoted away from the initial position shown in FIG. 9.

This ability to vary the frictional engaging force between the collar 30 and the hub 20 is advantageous in several respects, one of which is described here and another of which is described below. In the assembled condition shown in FIG. 9, the safety needle assembly must be connected to a fluid handling device such as a syringe. This requires rotation of the hub 20 so that the ridge 26 on the proximal end of the hub is able to be rotated to threadably engage (through a luer lock connection) the distal end of the syringe in the known manner. The connection of the safety needle assembly to the syringe can be done manually (if the safety needle assembly is packaged as is and subsequently connected to a syringe by the user) or in an automated manner (if the safety needle assembly is connected to a syringe by the manufacturer using automated equipment and then packaged for sale as syringe/safety needle assembly). In either case, with the safety needle assembly of the present invention, the protector 50 and the hub 20 rotate together as a unit when the safety needle assembly is in the assembled condition shown in FIG. 9 (i.e., when the protector 50 and the sheath 70 are in their initial positions) because the protector 50 is engaged with the collar 30 (by way of the cutouts 60, 62 in the protector 50 engaging the rib portions 36, 38 of the collar 30) and the collar 30 is prevented from rotating relative to the hub 20 (by virtue of the frictional engagement between the collar 30 and the hub 20 caused by the arms 75, 75 of the sheath 70 engaging the inclined outer side portions 43', 43' of the rib portion 36 of the collar 30). Thus, a rotational force applied to the protector 50 is transferred to the collar 30 which in turn is transferred to the hub 20 so that the ridge 26 on the hub 20 is rotated and can be threadably connected to the distal end of the syringe in a known manner. In effect, the protector 50 and the collar 30 rotate together as a unit when the protector 50 and the sheath 70 are in their initial positions (i.e., when the safety needle assembly is in the assembled condition).

In the absence of the frictional engagement between the collar 30 and the hub 20 sufficient to allow the hub 20 and the protector 50 to rotate together, another mechanism would be required to cause the hub 20 and the protector 50 to rotate together. For example, in the known needle assemblies described above in which a rigid cylindrical cap is mounted on the hub to cover the cannula, the inside surface of the cylindrical cap is provided with a plurality of longitudinally extending ridges. These ridges on the interior of the cylindrical cap are adapted to engage ridges on the exterior surface of the hub (e.g., ridges similar to the ridges 25 shown in FIG. 1) when a rotational force is applied to the cylindrical cap. In this way, a rotational force applied to the cylindrical cap is transferred to the hub so that the cylindrical cap and the hub rotate together as a unit. However, one difficulty associated with this construction is that the cylindrical cap must be carefully mounted on the hub to ensure that the ridges on the interior of the cylindrical cap are rotationally offset from the ridges on the hub as the cylindrical cap is mounted on the hub. Otherwise, as the cylindrical cap is being mounted on the hub, the ridges on the interior surface of the cylindrical cap will contact the ridges on the exterior surface of the hub and prevent the cylindrical cap from being mounted on the hub.

With the safety needle assembly of the present invention, the protector 50 and the hub 20 rotate together as a unit when the safety needle assembly is in the assembled condition shown in FIG. 9 by virtue of the frictional engagement between the collar 30 and the hub 20. Thus, the need for ridges on the interior of the protector, and the associated difficulties, are avoided or substantially eliminated.

In the assembled condition shown in FIG. 9, the safety needle assembly is ready for use. In the assembled condition shown in FIG. 9, the protector 50 is in its initial position in which the cannula secured to the hub 20 is at least partially surrounded or covered by the protector 50. In addition, the sheath 70 is in its initial position.

To use the safety needle assembly of the present invention, the assembled safety needle assembly shown in FIG. 9 is attached to a fluid transfer device, such as the distal end of a syringe barrel, through use of a known luer lock fitting utilizing the ridge 26 on the proximal end of the hub 20. As mentioned above, the safety needle assembly can be connected to a syringe at the time of manufacture or can be connected to a syringe by the user.

Figure 12:
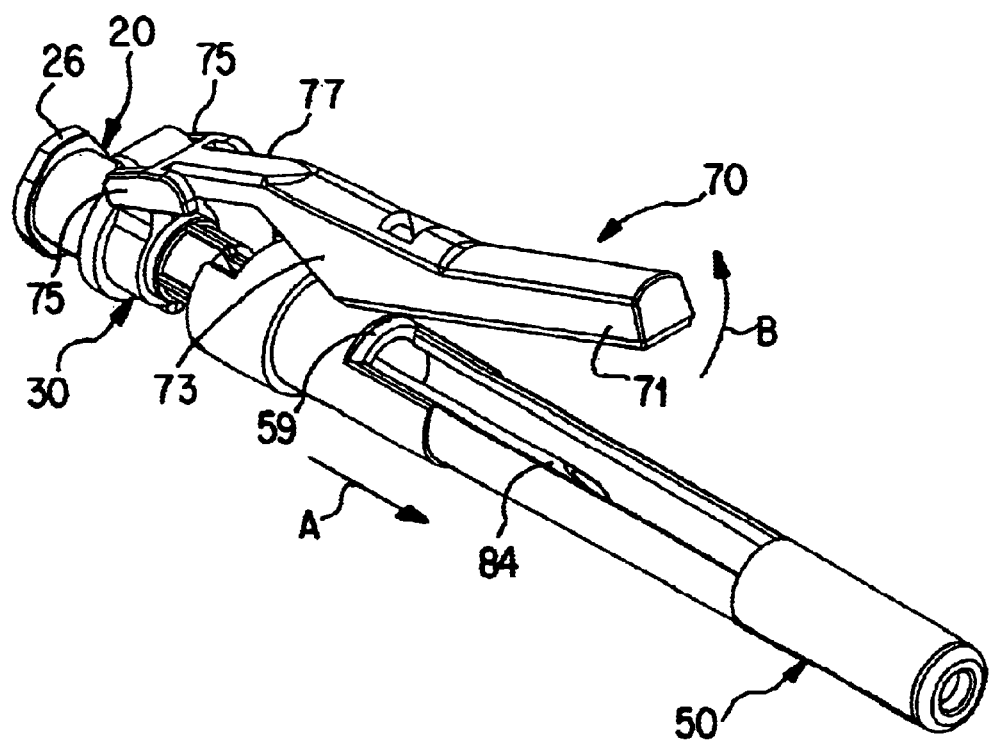
FIG. 12 is a perspective view of the safety needle assembly shown in FIG. 9 in which the protector has been moved towards the uncovering position.

To expose the cannula for usage, the protector 50 is grasped near its distal end 54 and is pulled axially or longitudinally away from the hub 20 and the collar 30, in the direction of the arrow A in FIG. 12, to thus move the protector 50 from the initial position shown in FIG. 9 toward a removed position or condition in which the cannula is uncovered by the protector 50. As shown in FIG. 12, as the protector 50 is moved axially towards the removed or uncovering position (in the direction of the arrow A), the sheath 70 is automatically pivoted away from the cannula and out of the opening 58 in the wall of the protector 50 (i.e., in the direction of the arrow B). This occurs by virtue of the protector 50 being provided with an engaging part that engages the sheath 70 in a way that forces the sheath 70 to pivot away from the cannula.

In this embodiment of the safety needle assembly, the engaging part of the protector 50 is defined by the edge 59 of the elongated opening 58 in the protector 50. As seen in FIG. 9, when the sheath 70 is in the initial position and the protector 50 is in the initial position (i.e., the safety needle assembly is in the assembled condition), the inclined surface of the intermediate portion 73 of the sheath 70 is spaced from the edge 59 of the opening 58 in the protector, but is located in the path of movement of the protector 50 as the protector 50 moves from the initial position toward the removed or uncovering position. Thus, when the protector 50 is moved in the direction of the arrow A in FIG. 12 from the initial position toward the removed position, the edge 59 of the opening 58 contacts the intermediate portion 73 of the sheath 70 and because the surface of the intermediate portion 73 of the sheath 70 is inclined, the sheath 70 is forced to automatically pivot away from the cannula 84 in the direction of the arrow B in FIG. 12 (i.e., towards an intermediate position).

Figure 13:
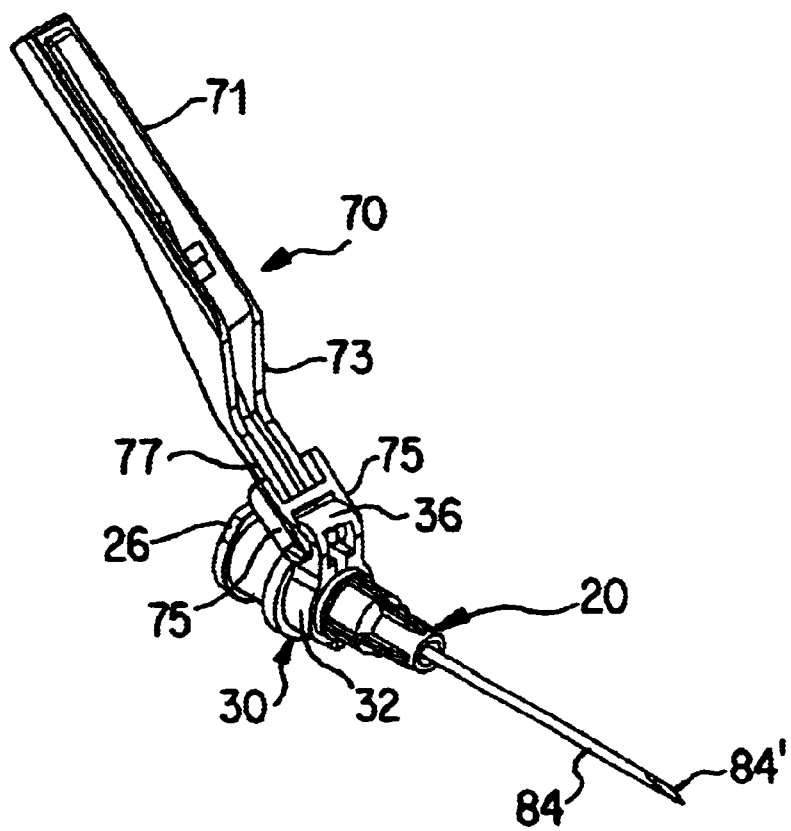
FIG. 13 is a perspective view of the safety needle assembly shown in FIG. 12 after the protector has been completely removed.

FIG. 13 illustrates the safety needle assembly once the protector 50 is completely removed. As can be seen, the sheath 70 has been pivoted away from the cannula 84 to leave the cannula 84 exposed and ready for use. It may be that when the protector is removed as described above to cause the sheath 70 to automatically pivot away from the protector and the cannula, the resulting position of the sheath 70 may not be the precise position shown in FIG. 13. That is, the amount of force applied to remove the protector may have a bearing on how far the sheath 70 pivots away from the cannula (i.e., whether the sheath pivots to a position similar to that shown in FIG. 12 or to a position similar to that shown in FIG. 13). In any event, once the protector 50 is removed, the sheath 70 can be pivoted further away from the cannula 84 manually, if desired.

With the protector removed and the sheath 70 pivoted away from the cannula so that the cannula 84 is exposed and ready for use (i.e., the intermediate position of the sheath 70), the arms 75, 75 on the sheath 70 are disengaged from the inclined surface portions 43', 43' of the rib portion 36 of the collar 30. Thus, in this position of the sheath 70 relative to the collar 30, the collar 30 is able to rotate relative to the hub 20 when a force is applied to the sheath 70. This is advantageous from the standpoint of allowing the user to position the sheath 70 at any desired position. It is oftentimes desirable to orient the cannula 84 so that the beveled edge 84' of the cannula 84 is oriented in a particular manner during usage. The rotatable nature of the collar 30 allows the sheath 70 be rotated to any desired position so that the sheath 70 does not interfere with the cannula, either visually or physically.

Figure 14:
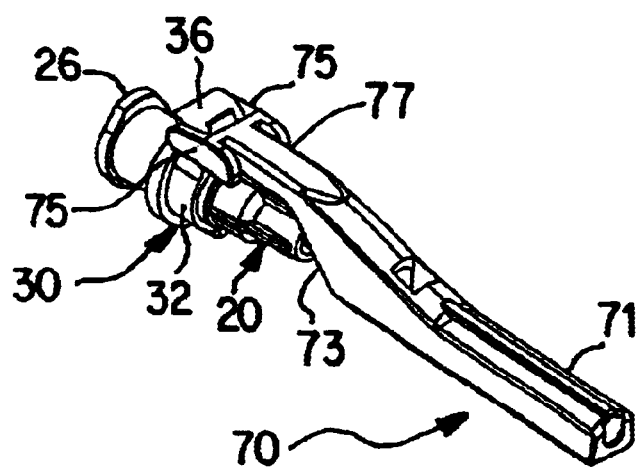
FIG. 14 is a perspective view of the safety needle assembly shown in FIG. 13 after the sheath has been moved to the cannula covering position.

Once the cannula 84 has been used for its intended purpose and has been removed from the patient, the sheath 70 can be pivoted by the user back towards the cannula 84 to a cannula covering position. In this cannula covering position which is illustrated in FIG. 14, the cannula 84 is received in the channel 81 of the sheath 70. The cannula retaining devices 86, 86 are able to automatically and permanently lockingly engage the cannula 84 in the channel 81 of the sheath 70.

The safety needle assembly is provided with a mechanism which helps facilitate an accurate determination that the cannula 84 is locked in the channel 81 of the sheath 70. As seen in FIG. 2, each of the holes 44, 44 in the rib portion 36 of the collar 30 is hexagonally shaped defining six flats in each of the holes 44, 44. Similarly, as shown in FIG. 4, each of the lugs 78, 78 extending from the respective arm 75, 75 of the sheath 70 is hexagonally shaped defining six flats on each of the lugs 78, 78. As the sheath 70 is pivoted so that the lugs 78, 78 of the sheath 70 rotate within the holes 44, 44 in the collar 30, there will be a natural tendency for the lugs 78, 78 to assume a position within the holes 44, 44 in which the flats on the lugs 78, 78 are aligned with or face the flats in the holes 44, 44. That is, if a force is applied to the sheath 70 to pivot the sheath and then the force is removed, the sheath 70 will tend to move to a position in which the flats on the lugs 78, 78 are aligned with or face the flats in the holes 44, 44. The flats in the holes 44, 44 of the collar 30 are oriented relative to the flats on the lugs 78, 78 of the sheath 70 so that when the sheath 70 is in the locked condition in which the cannula 84 is lockingly engaged by the cannula retaining devices 86, 86 and is locked within the channel of the sheath 70, the flats on the lugs 78, 78 are not aligned with the flats in the holes 44, 44 of the collar 30. Thus, if the sheath 70 is pivoted towards the cannula covering position, but is not pivoted sufficiently far to cause the cannula retaining devices 86, 86 of the sheath 70 to lockingly engage the cannula 84, the sheath 70 will tend to pivot backwards away from the cannula 84 to a position in which the flats on the lugs 78, 78 are aligned with or face the flats in the holes 44, 44 of the collar 30. The cannula 84 will thus not be positioned within the channel in the sheath 70, thus providing an indication that the cannula engaging devices 86, 86 have not lockingly engaged the cannula and that the sheath 70 is not in the locked condition.

Figure 15:
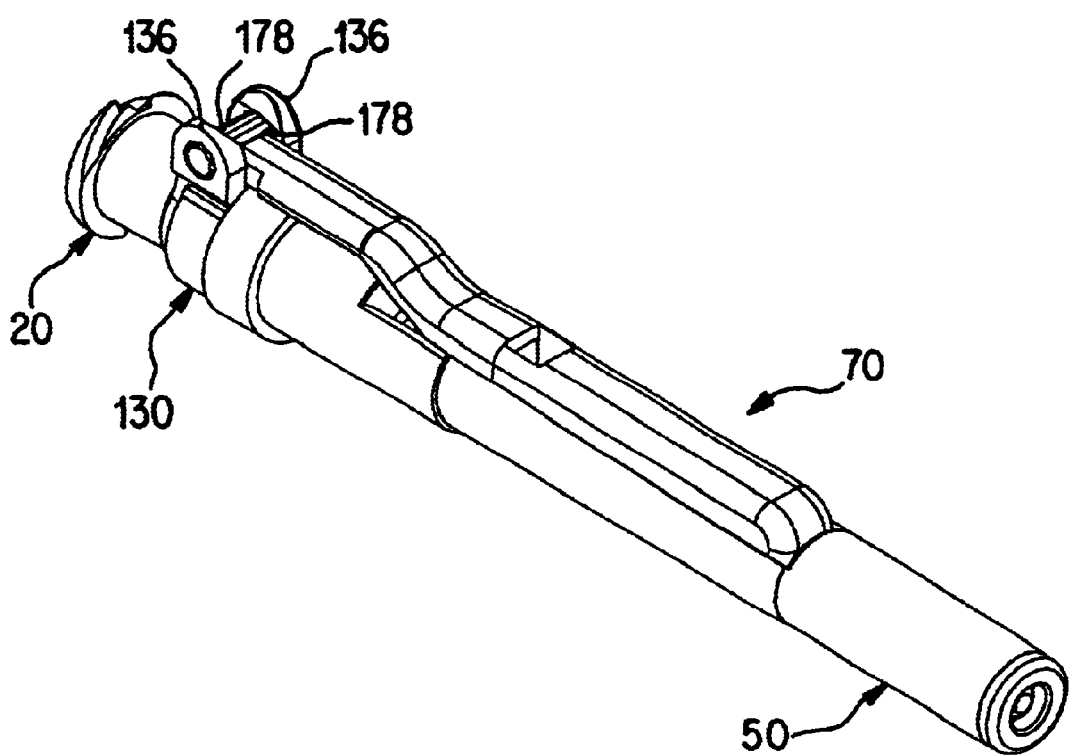
FIG. 15 is a perspective view of the safety needle assembly according to another embodiment of the present invention in the assembled state.

FIG. 15 illustrates an alternative to the embodiment of the safety needle assembly described above in that it utilizes a slightly different collar and a slightly different connecting portion on the sheath. In the embodiment shown in FIG. 15, the collar 130 is provided with a pair of spaced apart upstanding rib portions 136, 136 and the connecting portion of the sheath 70 is provided with a pair of outwardly extending lugs 178, 178. Thus, rather than engaging the holes in the rib portion of the collar from the outside as in the embodiment described above, the lugs 178, 178 engage the holes in the rib portions 136, 136 of the collar 130 from the inside.

In this embodiment, the lugs 178, 178 and the holes in the rib portions 136, 136 can also be provided with flats as described above to help facilitate determining that the cannula is locked in the channel of the sheath. Also, in this embodiment shown in FIG. 15, rotation of the protector can be transferred to the hub for purposes of, for example, connecting the assembly to a syringe by providing the inner surface of the protector with spaced apart ribs that are located between spaced apart ribs on the exterior of the hub. Upon applying a rotation force to the protector, the ribs on the inner surface of the protector engage the ribs on the exterior surface of the hub, thus causing the rotation force to be transferred from the protector to the hub.

Figure 16:
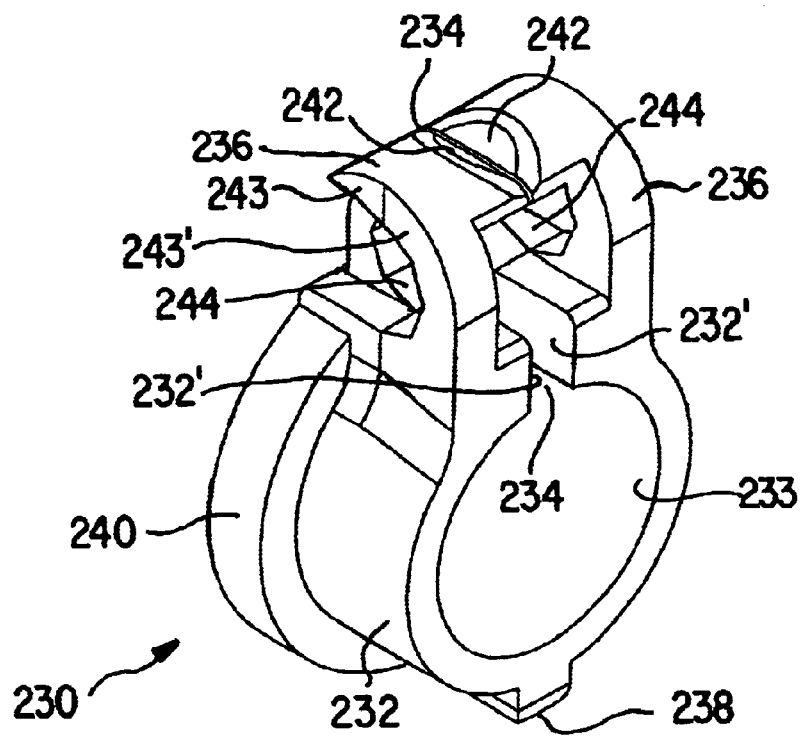
FIG. 16 is a perspective view of an alternative embodiment of the collar than can be used in the safety needle assembly shown in FIGS. 1–14
Figure 17:
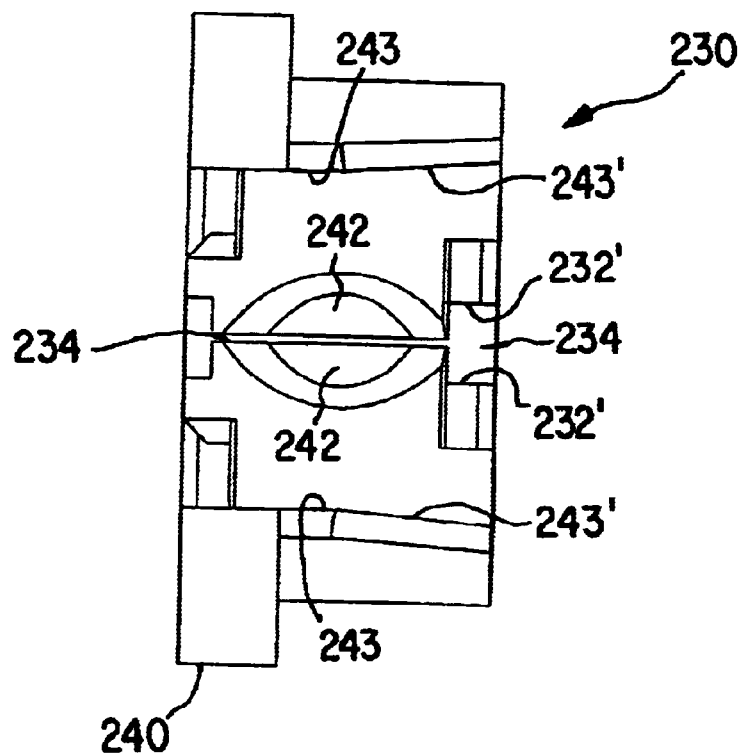
FIG. 17 is a top plan view of the collar shown in FIG. 16.

FIGS. 16 and 17 illustrate another embodiment of the collar than can be used as an alternative to the collar shown in FIGS. 2 and 7. In the version of the collar 230 shown in FIGS. 16 and 17, the collar 230 includes a generally annular or ring shaped portion 232, which defines a centrally located hole 233, and two upstanding rib members 236, 236 that are separated by a split 234 and together form a rib portion of the collar. By virtue of the split 234, the two rib members 236, 236 can be urged away from one another upon application of a force tending to spread the two rib members 236, 236 apart. Each of the rib members 236, 236 is provided with a pair of laterally extending through holes 244, 244 that are configured in the same manner as the holes in the rib portion shown in FIG. 2 and described above. The annular portion 232 is provided with a split 234 defining circumferentially spaced apart ends 232', 232' of the annular portion 232.

The collar 230 is also provided with a second radially outwardly directed rib portion 238 positioned diametrically opposite the first rib portion defined by the two rib member 236, 236. In a manner similar to that described above in connection with the first embodiment, the first rib portion defined by the two rib members 236, 236 possesses a greater width than the second rib portion 238. The collar 230 further includes a radially outwardly directed ridge 240 at the proximal end of the collar 230.

Each of the rib members 236, 236 possesses a laterally outwardly facing side surface 243, 243. As illustrated in FIG. 17, at least a portion 243', 243' of each side surface 243, 243 is slightly inclined outwardly so that the side surface portions 243', 243' diverge away from one another in a direction away from the ridge 240. In the illustrated embodiment, the outward inclination of the side surface portions 243', 243' begins at a point on each rib member 236, 236 located forward of the ridge 240. In a manner similar to that described above, the outward angle of inclination of the side surface portions 243', 243' can be on the order of approximately 5°, although variations are possible. The purpose for the inclined side surface portions 243', 243' of the collar 230 is the same as that described above.

Also, as can be seen in FIG. 16, each of the rib members 236, 236 is provided with an angled or sloping top edge 242, 242 which together define an indented region at the top of the rib portion defined by the two rib members 236, 236.

The collar 230 shown in FIGS. 16 and 17 is adapted to be mounted at the recessed region 28 of the hub 20 in a manner slightly different from the way in which the collar shown in FIGS. 2 and 7 is mounted at the recessed region 28 of the hub 20. The mounting of the collar 230 on the recessed region 28 of the hub 20 can be accomplished by positioning the indented region of the collar 230 defined by the angled top edges 242, 242 of the rib members 236, 236 against the recessed region 28 of the hub 20. Applying a suitable force pressing the collar 230 towards the hub 20 causes the rib members 236, 236 on either side of the split 234 to spread apart, thus allowing the collar 230 to snap into place on the recessed region 28 of the hub 20 so that the hub 20 is received in the hole 233 in the collar 230. The indented region of the collar 230 defined by the angled top edges 242, 242 of the rib members 236, 236 thus facilitates proper location or positioning of the collar 230 relative to the hub 20 and also assists in initially urging apart the rib members 236, 236 located on either side of the split 234. In addition, the outwardly inclined side surface portions 243', 243' on the rib members 236, 236, in cooperation with the arms of the sheath, provide a mechanism for varying the frictional engaging force between the collar 230 and the hub 20 depending upon the position of the sheath in the same manner as described above with respect to the first embodiment of the invention.

Using the version of the collar shown in FIGS. 16 and 17, the safety needle assembly can be assembled in an appropriate manner. For example, after the cannula is fixed to the distal end of the hub, the collar 230 is mounted onto the hub in the manner described above (or alternatively by being axially slid onto the hub from the distal end of the hub). The protector is then inserted over the cannula and pressed onto the collar. The sheath can then be attached to the collar and subsequently pivoted to the initial position in which the sheath extends into the opening in the wall of the protector. The safety needle assembly is thus in the assembled condition.

Figure 18:
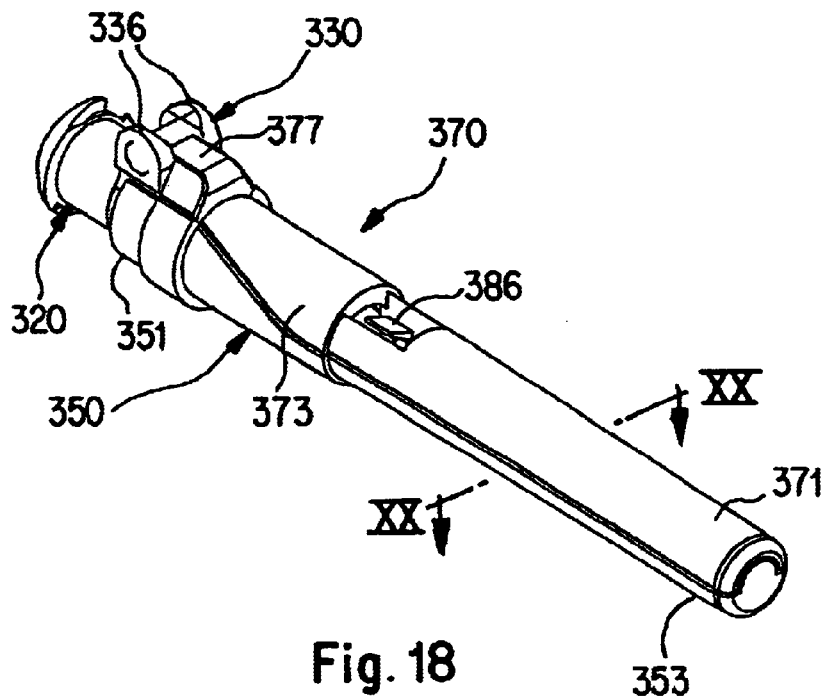
FIG. 18 is a perspective view of a safety needle assembly according to another embodiment of the invention in the assembled condition.
Figure 19:
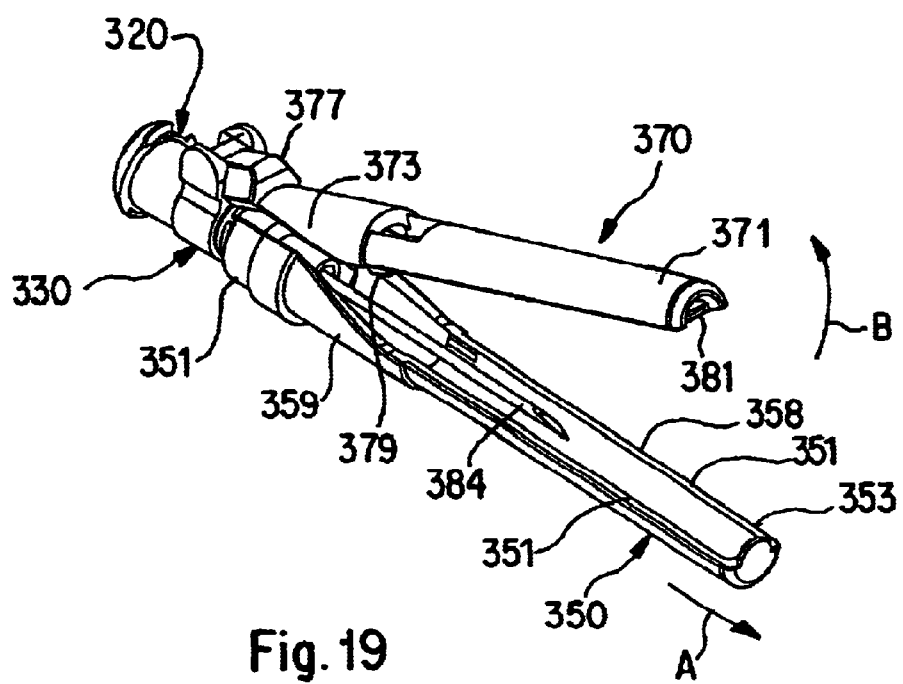
FIG. 19 is a perspective view of the safety needle assembly shown in FIG. 18 in which the protector has been moved towards the uncovering position.
Figure 20:
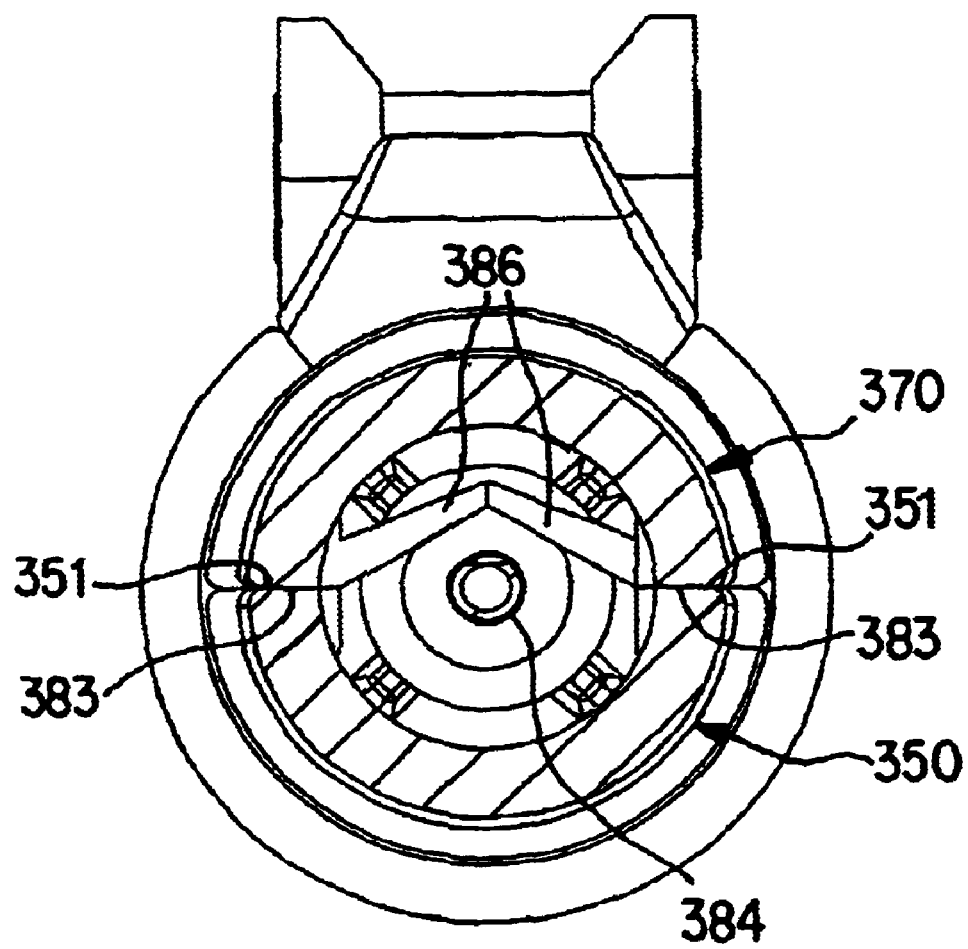
FIG. 20 is a cross-sectional view of the safety needle assembly shown in FIG. 18 taken along the section line X—X in FIG. 18.

FIGS. 18–20 illustrate an alternative embodiment of the safety needle assembly according to the present invention, with FIG. 18 illustrating the safety needle assembly in the assembled condition and FIG. 19 illustrating the safety needle assembly as the protector is moved from the initial position toward the uncovering or removed position. The safety needle assembly shown in FIGS. 18–20 includes a hub 320, a collar 330, a protector 350 and a sheath 370. The hub 320 is configured in a manner similar to that described above in connection with the first embodiment, and the collar 330 is rotationally mounted on a recessed portion of the hub 320. The collar 330 is configured in a manner similar to the collar 130 shown in FIG. 15 in that the collar 330 includes two spaced apart upstanding rib members 336, 336 which together define a rib portion of the collar 330. The sheath 370 is pivotally connected to the collar 330 by way of two outwardly extending lugs on the collar connecting end of the sheath 370 that engage respective holes in the upstanding rib members 336, 336 of the collar 330.

As seen in FIG. 19, the protector 350 is elongated and provided with an opening 358 communicating with the interior of the protector 350. The opening 358 in this embodiment extends along the entire longitudinal extent of the protector 350 from the proximal end to the distal end. The protector 350 is mounted on the collar 330 so that the rib portion of the collar defined by the rib members 336, 336 is positioned within the proximal end portion of the opening 358. The proximal end portion 351 of the protector 350 is generally C-shaped as seen in cross-section and has a circumferential extent greater than the circumferential extent of the distal end portion 353 of the protector 350. An intermediate portion of the protector 350 defines an engaging part 359 of the protector 350 that is adapted to engage the sheath 370 when the protector is axially or longitudinally moved.

The sheath 370 which is pivotally connected to the collar 330 is provided with cannula engaging projections 386, 386 as seen in FIG. 20 that are adapted to automatically and permanently lockingly engage the cannula 384 to lock the sheath in the cannula covering position. The sheath 370 possesses a channel, defined by side walls and a back wall of the sheath, that receives the cannula 384 when the sheath 370 is in the cannula covering position.

As seen in FIG. 19, the sheath 370 is provided with at least one tab 379 on each longitudinally extending side of the sheath 370. These tabs 379 are adapted to engage corresponding catches on the sides of the protector 350 when the safety needle assembly is in the assembled condition shown in FIG. 18. In addition, the distal end of the sheath 370 is provided with a catch 381 that is adapted to mate with a tab on the distal end of the protector 350 when the safety needle assembly is in the assembled condition shown in FIG. 18. The tabs and the catches on the sheath 370 and the protector 350 help maintain the sheath 350 and the protector 370 in the assembled condition shown in FIG. 18 and prevent the sheath 370 from freely pivot away from the illustrated initial position in the absence of a pivoting force applied to the sheath 370.

As further seen in FIGS. 19 and 20, the protector 350 is provided with longitudinally extending edge surfaces 351 extending from the proximal end of the protector 350 to the distal end of the protector 350. Similarly, as seen in FIG. 20, the sheath 370 includes longitudinally extending edge surfaces 383, 383 that extend between the proximal and distal ends of the sheath 370. As illustrated in FIGS. 18 and 20, when the safety needle assembly is in the assembled condition, the longitudinally extending edge surfaces 351, 351 on the protector 350 face and preferably engage the longitudinally extending edge surfaces 383, 383 on the sheath 370. In the assembled condition illustrated in FIG. 18, the outer surface of the protector 370 forms a portion of a cylindrical surface while the outer surface of the protector 350 also forms a portion of a cylindrical surface. Together, the outer surface of the protector 350 and the outer surface of the sheath 370 form a cylindrical surface, with the sheath 350 and the protector 370 together defining a cylindrical element.

To use the safety needle assembly in the assembled condition illustrated in FIG. 18, the protector 350 is grasped and pulled longitudinally or axially in the direction of the arrow A in FIG. 19 to move the protector from the initial position towards a removed or uncovering position. As the protector 350 is moved in this manner, the inclined portion or engaging part 359, 359 of each longitudinal edge surface 351, 351 of the protector 350 acts against the facing inclined edge surface of the intermediate portion 373 of the sheath 370, thus causing the sheath 370 to automatically pivot away from the cannula 384 and the protector 350 in the direction of the arrow B in FIG. 19. In this way, when the protector 350 is moved longitudinally or axially in the direction of the arrow A to move the protector 350 from the initial position toward the uncovering or removed position, the sheath 370 is automatically pivoted away from the cannula 384 and the protector 370, and is moved to an intermediate position. Thereafter, in a manner similar to that described above, the sheath 370 can be manually pivoted back towards the cannula 384 to a cannula covering position in which the cannula engaging projections 386, 386 engage the cannula and thus permanently lock the sheath 370 in a position which covers the cannula 384. In this embodiment, rotation of the protector can be transferred to the hub for purposes of connecting the assembly to a syringe by providing the inner surface of the protector with spaced apart ribs that are located between spaced apart ribs on the exterior of the hub. When a rotation force is applied to the protector, the ribs on the inner surface of the protector engage or come into contact with the ribs on the exterior surface of the hub, thus causing the rotation force to be transferred from the protector to the hub.

FIGS. 21–24 illustrate a further embodiment of the safety needle assembly of the present invention. This embodiment of the safety needle assembly also includes a hub 420, a collar 430, a protector 450 and a sheath 470. The collar 430 is rotatably mounted on a recessed portion of the hub 420 and includes two spaced apart upstanding rib members which together define a rib portion of the collar 430. The sheath 470 is pivotally connected to the collar 430 by way of two outwardly extending lugs on the collar connecting end of the sheath 470 that engage respective holes in the upstanding rib members of the collar 430.

Figure 21:
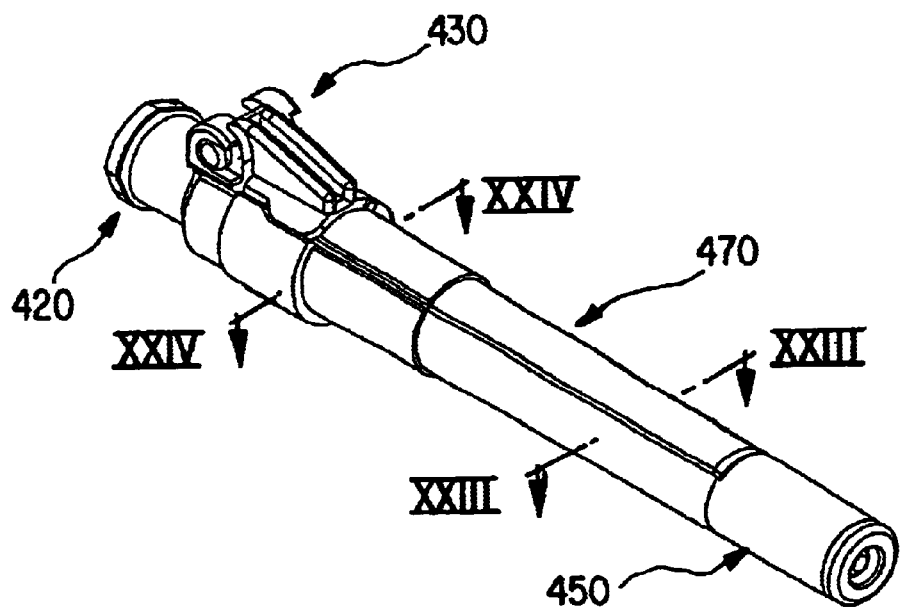
FIG. 21 is a perspective view of a safety needle assembly according to another embodiment of the invention in the assembled condition.
Figure 22:
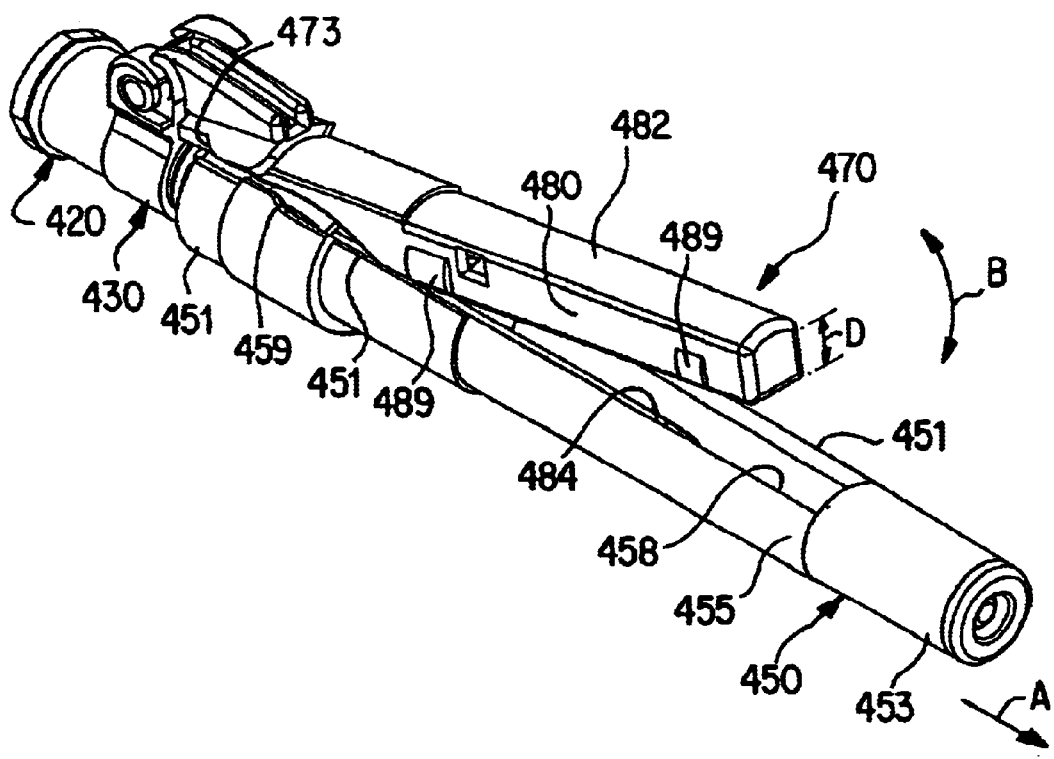
FIG. 22 is a perspective view of the safety needle assembly shown in FIG. 21 in which the protector has been moved towards the uncovering position.
Figure 24:
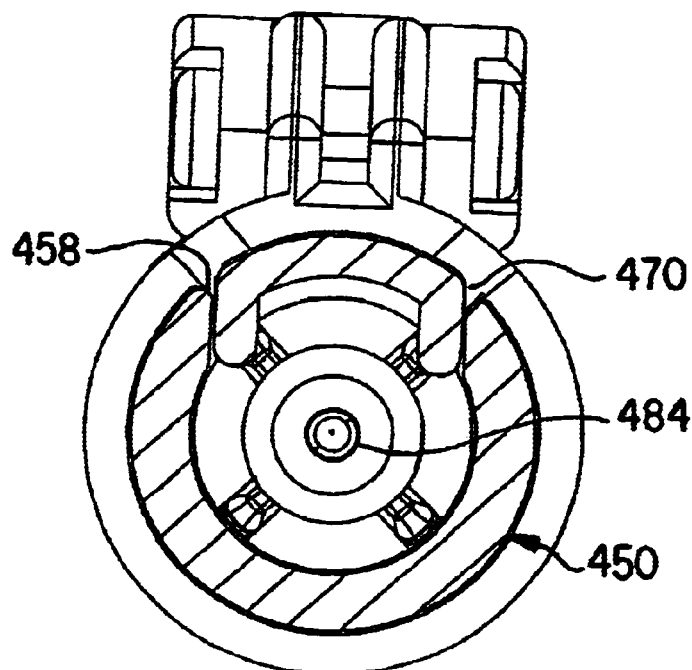
FIG. 24 is a cross-sectional view of the safety needle assembly shown in FIG. 21 taken along the section line XIV—XIV in FIG. 21.

The protector 450 is mounted on the collar 430 and is provided with a longitudinally extending opening 458. The longitudinally extending opening 458 opens to the proximal end portion 451 of the protector 450, but stops short of the distal end portion 453 of the protector 450 as shown in FIG. 22. The protector 450 is mounted on the collar 430 so that the rib portion of the collar is positioned within the proximal end portion of the opening 458 in the protector 450. As also illustrated in FIGS. 21 and 22, the size or circumferential extent of the opening 458 in the protector 450 is slightly smaller at the proximal end portion 451 of the protector than at the opposite end. Thus, the circumferential extent of the protector 450 at the proximal end portion 451 is slightly greater than the circumferential extent of the protector 450 at the portion 455 located adjacent the distal end of the opening 458.

The protector 450 possesses longitudinally extending edge surfaces 451. An inclined portion 459 of each edge surface 451 forms an engaging part of the protector 450 that is adapted to engage a respective inclined edge portion 473 of the sheath 470 and pivot the sheath 470 away from the protector 450 and the cannula 484 when the protector 450 is moved longitudinally or axially away from the collar 430.

Figure 23:
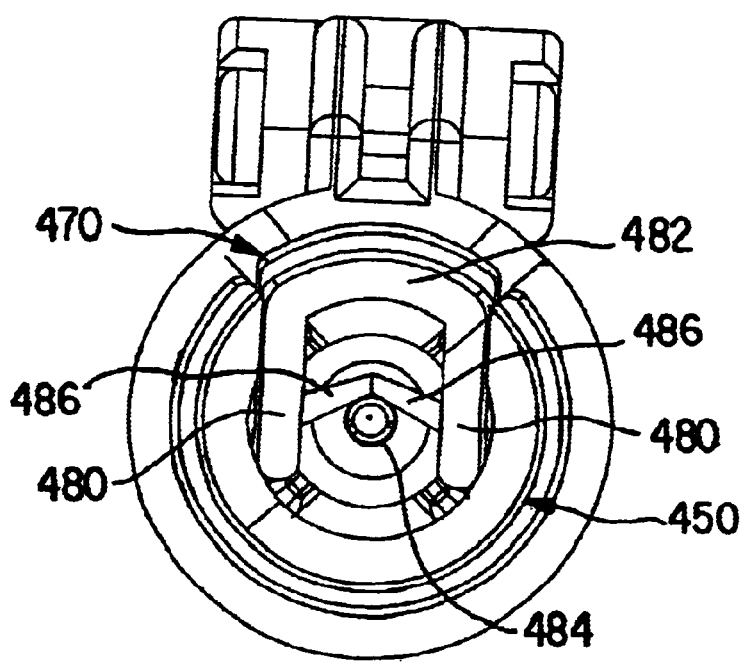
FIG. 23 is a cross-sectional view of the safety needle assembly shown in FIG. 21 taken along the section line XIII—XIII in FIG. 21.

The sheath 470 is pivotally connected to the collar 430 by virtue of lugs on the sheath 470 that engage holes provided in the upstanding rib members of the collar 430. The sheath 470 includes a cannula receiving channel defined by side walls and a back wall of the sheath 470. In addition, as seen in FIG. 23, the sheath 470 is provided with cannula engaging projections 486, 486 that are adapted to lockingly engage the cannula 484 when the sheath 470 is pivoted to a sufficient extent. The sheath 470 is also provided with outwardly directed projections 489 on both of the side walls of the sheath 470. These projections 489, which may be somewhat rounded as illustrated in FIG. 22, help keep the sheath 470 within the opening 485 in the assembled condition of the safety needle assembly.

In the assembled condition of the safety needle assembly shown in FIG. 21, the side walls 480 of the sheath 470 are positioned within the opening 458 in the protector 450. As seen in FIG. 22, the depth of the sidewalls 480 (i.e., the dimension D of the sidewalls 480 shown in FIG. 22) gradually diminishes towards the proximal end of the sheath 470 until a point where the side walls 480 no longer exist. At the proximal end portion of the sheath 470 and the proximal end portion of the protector 450, the longitudinally extending edges of the protector 450 and the sheath 470 face one another as seen in FIG. 22. In particular, the inclined engaging edge surface portions of the protector 450 defining the engaging parts 459 of the protector 450 face the inclined engaging edge surface portions 473 on the sheath 470.

Also, in the assembled condition of the safety needle assembly (i.e., when the sheath and the protector are in their initial positions), the tip ends of the side walls 480, 480 contact the inner surface of the protector 450 as shown in FIG. 23. Thus, when the safety needle assembly is in the assembled condition, the sheath 470 is prevented from being pivoted to a position in which the cannula engaging projections 486, 486 lockingly engage the cannula 486 and lock the sheath 470 in position.

To use the safety needle assembly in the assembled condition shown in FIG. 21, the protector 450 is longitudinally or axially moved away from the collar 430 in the direction of the arrow A in FIG. 22. During this movement of the protector 450 from the initial position towards the uncovering or removed position, the inclined engaging part 459 of the protector 450 acts against the inclined engaging part 473 of the sheath 470 to thereby cause the protector 470 to automatically rotate in the direction of the arrow B in FIG. 22. The sheath 470 is thus automatically pivoted from the initial position shown in FIG. 22 in a direction away from the protector 450 and the cannula 484 towards an intermediate position. Once the protector 450 has been moved from the initial position to the uncovering or removed position in which the cannula 484 is exposed, the sheath 470 can be manually pivoted back towards the cannula 484 until the cannula retaining projections 486, 486 lockingly engage and trap the cannula 484, thereby locking the sheath 470 in the cannula covering position. In this embodiment, rotation of the protector 450 can be transferred to the hub 420 for purposes of connecting the assembly to a syringe by providing the inner surface of the protector 450 with spaced apart ribs that are located between spaced apart ribs on the exterior of the hub 420 when the protector is in the initial condition. When a rotation force is applied to the protector, the ribs on the inner surface of the protector 450 engage or come into contact with the ribs on the exterior surface of the hub 420, thus causing the rotation force to be transferred from the protector to the hub.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A safety needle assembly comprising:
   a hub having a proximal end adapted to be connected to a fluid transfer device and a distal end;
   a cannula having a proximal end connected to the hub and a distal end;
   a collar mounted on the hub;
   a protector having an interior, the protector being movable between an initial position in which the cannula is at least partially covered by the protector and a removed position in which the cannula is uncovered by the protector, said protector including a through opening;
   a sheath pivotally mounted on the collar and positioned in an initial position in which the through opening in the protector is closed by the sheath, the sheath including a longitudinally extending channel, the sheath being adapted to pivot from the initial position in a direction away from the cannula to permit use of the cannula and being adapted to pivot back towards the cannula to a cannula covering position in which the cannula is located within the channel of the sheath;
   the protector being provided with an engaging part that engages the sheath during movement of the protector from the covering position toward the removed position to cause the sheath to automatically pivot away from the initial position; and
   means for permanently locking the sheath in the cannula covering position.

2. The safety needle assembly according to claim 1, wherein the sheath includes at least one lug provided with a plurality of flat surfaces and the collar includes at least one hole provided with a plurality of flat surfaces, the at least one lug of the sheath being positioned in the at least one hole of the collar.

3. The safety needle assembly according to claim 1, wherein the sheath includes a proximal end portion provided with a pair of lugs positioned in opposing relation to one another and extending towards one another, the collar comprising a rib portion and a split annular portion defining two circumferentially spaced apart ends of the annular portion, the rib portion possessing a pair of holes and each of the lugs being positioned in one of the holes.

4. The safety needle assembly according to claim 3, wherein the sheath includes a pair of spaced apart arms, each of the lugs extending from one of the arms, the rib portion of the collar having outwardly facing side surfaces, at least a portion of each of the outwardly facing side surfaces of the rib portion being angled outwardly in a direction towards the distal end of the hub so that frictional engagement between the collar and the hub when the sheath is in the initial position is greater than the frictional engagement between the collar and the hub when the sheath is pivoted away from the cannula.

5. The safety needle assembly according to claim 1, wherein the protector includes a proximal end that engages the collar so that the protector is mounted on the collar.

6. The safety needle assembly according to claim 5, wherein the collar is provided with first and second rib portions circumferentially spaced apart from one another, with one of the rib portions having a greater width than the other rib portion, and the protector being provided with first and second spaced apart cutouts at the proximal end of the protector, with one of the cutouts having a greater circumferential extent than the other cutout, the protector being mounted on the collar with the first rib portion located in the first cutout and the second rib portion located in the second cutout so that the protector is adapted to be mounted on the collar in only one rotational orientation.

7. The safety needle assembly according to claim 6, wherein the through opening in the protector is circumferentially aligned with one of the rib portions.

8. The safety needle assembly according to claim 1, wherein the collar is rotationally mounted on the hub.

9. The safety needle assembly according to claim 1, wherein the sheath includes a proximal end provided with a pair of lugs extending away from one another, the collar including a pair of spaced apart rib portions each provided with a hole, each of the lugs being positioned in one of the holes.

10. The safety needle assembly according to claim 1, wherein the engaging part of the protector includes a periphery of the through opening in the protector, the sheath having an inclined surface that is engaged by the periphery of the through opening in the protector during movement of the protector from the covering position toward the removed position.

11. The safety needle assembly according to claim 1, wherein the through opening in the protector extends from a proximal end of the protector to a distal end of the protector, the protector including longitudinally extending edge surfaces and the sheath including longitudinally extending edge surfaces, each of the edge surfaces of the sheath facing one of the edge surfaces of the protector when the sheath is in the initial position and the protector is in the initial position, the engaging part of the protector including a portion of each of the edge surfaces of the protector being inclined and engaging inclined portions of the edge surfaces of the sheath during movement of the protector from the covering position toward the removed position.

12. The safety needle assembly according to claim 1, wherein the through opening in the protector extends along only a portion of a longitudinal extent of the protector, the protector including longitudinally extending edge surfaces that face longitudinally extending edge surfaces of the sheath adjacent proximal end portions of the sheath and protector, at least a portion of the sheath extending through the through opening in the protector and being located within the interior of the protector when the sheath and the protector are in the initial positions, the engaging part of the protector including inclined portions of the edge surfaces of the protector, the inclined portions of the edge surface of the protector engaging inclined portions of the edge surfaces of the sheath during movement of the protector from the covering position toward the removed position.

13. The safety needle assembly according to claim 1, wherein the sheath includes oppositely positioned side walls and a back wall that together define the channel in the sheath, portions of the side walls of the sheath extending through the through opening in the protector and into the interior of the protector when the sheath is in the initial position.

14. A safety needle assembly comprising:

a hub having a proximal end adapted to be connected to a fluid transfer device and a distal end;

a cannula having a proximal end connected to the hub and a distal end;

a protector having an interior, the protector being positioned in an initial position in which the protector at least partially covers the cannula, the protector being adapted to be removed so that the cannula is uncovered by the protector, the protector including an opening that communicates with the interior of the protector;

a sheath pivotally mounted with respect to the hub and configured to define a channel;

at least one cannula engaging projection provided on the sheath and extending into the channel;

the sheath being positioned in an initial position in which at least a portion of the sheath extends through the opening in the protector and into the interior of the protector, the sheath being adapted to pivot away from the cannula and out through the opening in the protector and being adapted, after the protector is removed, to pivot back towards the cannula to a cannula locking position in which the cannula is lockingly engaged by the at least one cannula engaging projection; and means for preventing the cannula engaging projection from lockingly engaging the cannula when the sheath is in the initial position.

15. The safety needle assembly according to claim 14, wherein the sheath is pivotally mounted on a collar, the collar being mounted on the hub.

16. The safety needle assembly according to claim 15, wherein the sheath includes a proximal end portion provided with a pair of lugs positioned in opposing relation to one another and extending towards one another, the collar comprising an annular split portion and a rib portion, the rib portion possessing at least one hole and the lugs being positioned in the hole.

17. The safety needle assembly according to claim 16, wherein the sheath includes a pair of spaced apart arms, each of the lugs extending from one of the arms, the rib portion of the collar having outwardly facing side surfaces, at least a portion of each of the outwardly facing side surfaces of the rib portion being angled outwardly in a direction towards the distal end of the hub so that frictional engagement between the collar and the hub when the sheath is in the initial position is greater than the frictional engagement between the collar and the hub after the sheath has been pivoted away from the initial position.

18. The safety needle assembly according to claim 15, wherein the protector includes a proximal end that engages the collar.

19. The safety needle assembly according to claim 18, wherein the collar is provided with first and second rib portions circumferentially spaced apart from one another, with one of the rib portions having a greater width than the other rib portion, and the protector being provided with first and second spaced apart cutouts at the proximal end of the protector, with one of the cutouts having a greater circumferential extent than the other cutout, the protector being mounted on the collar with the first rib portion located in the first cutout and the second rib portion located in the second cutout so that the protector is mountable on the collar in only one rotational orientation.

20. The safety needle assembly according to claim 19, wherein the opening in the protector is circumferentially aligned with one of the rib portions.

21. The safety needle assembly according to claim 14, wherein the sheath is pivotally mounted on a collar that encircles the hub, the collar being rotatable with respect to the hub when the sheath is pivoted away from the cannula.

22. The safety needle assembly according to claim 14, wherein the sheath includes a proximal end provided with a pair of lugs extending away from one another, the collar including a pair of spaced apart rib portions each provided with a hole, each of the lugs being positioned in one of the holes.

23. The safety needle assembly according to claim 14, wherein the opening in the protector is surrounded by a wall that engages a portion of the sheath as the protector is removed.

24. The safety needle assembly according to claim 14, wherein the opening in the protector extends along less than the entire longitudinal extent of the protector, the protector including longitudinally extending edge surfaces that face longitudinally extending edge surfaces of the sheath adjacent proximal end portions of the sheath and the protector, the sheath being positioned relative to the protector so that at least a portion of the sheath is located within an interior of the protector when the sheath is in the initial position, the protector having an engaging part that engages a portion of the sheath as the protector is removed and automatically pivots the sheath away from the cannula, the engaging part of the protector being formed by an inclined portion of each of the edge surfaces of the protector, the inclined portion of each of the edge surfaces of the protector being adapted to engage a respective inclined portion of the edge surfaces of the sheath during removal of the protector.

25. The safety needle assembly according to claim 14, wherein the sheath is pivotally connected to a collar that is mounted on the hub, and including means for reducing a friction force between the collar and the hub when the sheath is pivoted away from the initial position in a direction away from the cannula.

26. The safety needle assembly according to claim 14, wherein the means for preventing the cannula engaging projection from engaging the cannula when the sheath is in the initial position includes a portion of the sheath contacting an interior surface of the protector.

27. A safety needle assembly comprising:
   a hub having a proximal end adapted to be connected to a fluid transfer device and a distal end;
   a cannula having a proximal end connected to the hub and a distal end;
   a collar mounted on the hub;
   a protector mounted on the collar, the protector being movable from an initial position in which the protector at least partially surrounds the cannula toward a removed condition in which the cannula is uncovered by the protector, the protector including a through opening;
   a sheath pivotally mounted on the collar and positioned in an initial position in which the through opening in the protector is closed by the sheath, the sheath including a longitudinally extending channel, the sheath being adapted to be pivoted from the initial position in a direction away from the cannula and being adapted to be pivoted in a direction back towards the cannula to a cannula covering position in which the cannula is located within the channel of the sheath;
   means for locking the sheath in the cannula covering position; and
   the collar including at least one surface portion which is engaged by a portion of the sheath when the sheath is in the initial position to produce a first frictional engaging force between the collar and the hub sufficient to cause the collar and the hub to rotate together as a unit and which is disengaged from the portion of the sheath when the sheath is pivoted away from the initial position to reduce the frictional engaging force between the collar and the hub to permit the collar to rotate relative to the hub.

28. The safety needle assembly according to claim 27, wherein the at least one surface portion of the collar is an inclined outwardly facing surface of the collar.

29. The safety needle assembly according to claim 27, wherein the collar includes a rib portion and a split annular ring portion having circumferentially spaced apart ends, the at least one surface portion including a pair of surface portions each forming a portion of an outwardly facing side surface of the rib portion.

30. The safety needle assembly according to claim 29, wherein the surface portions are angled outwardly away from one another and are engaged by a portion of the sheath when the sheath is in the initial position to urge the circumferentially spaced apart ends of the split annular ring portion towards one another to produce the first frictional engaging force.

31. The safety needle assembly according to claim 27, wherein the means for locking the sheath in the cannula covering position includes at least one cannula engaging projection that lockingly engages the cannula, and including means for preventing the cannula engaging projection from lockingly engaging the cannula when the sheath is in the initial position.

32. The safety needle assembly according to claim 31, wherein the means for preventing the cannula engaging projection from engaging the cannula when the sheath is in the initial position includes a portion of the sheath contacting an interior surface of the protector when the sheath is in the initial position.

33. The safety needle assembly according to claim 27, wherein the protector includes an engaging part that engages a portion of the sheath as the protector is moved toward the removed condition to cause the sheath to automatically pivot away from the initial position of the sheath.

34. A safety needle assembly comprising:
   a hub having a proximal end adapted to be connected to a fluid transfer device and a distal end;
   a cannula having a proximal end connected to the hub and a distal end;
   a collar mounted on the hub;
   a protector mounted on the collar in an initial position in which the protector at least partially covers the cannula, the protector being movable to separate the protector from the collar so that the cannula is uncovered by the protector the protector including a through opening;
   a sheath pivotally mounted on the collar and positioned in an initial position in which the through opening in the protector is closed by the sheath, the sheath including a longitudinally extending channel, the sheath being adapted to pivot from the initial position in a direction away from the cannula and being adapted to pivot back towards the cannula to a cannula covering position in which the cannula is located within the channel of the sheath; and
   the protector and the sheath each having an outer surface configured as a part of a cylinder, the protector and the sheath together defining a cylindrical outer surface when the protector is in the initial position and the sheath is in the initial position.

35. The safety needle assembly according to claim 34, wherein the outer surface of the sheath possess a radius of curvature that is the same as the radius of curvature of the outer surface of the protector.

36. The safety needle assembly according to claim 34, wherein the sheath includes side walls defining sides of the longitudinally extending channel, the side walls extending through the opening in the protector when the sheath is in the initial position.

37. The safety needle assembly according to claim 34, wherein the sheath includes at least one cannula retaining projection that is adapted to lockingly engage the cannula to lock the sheath in the cannula covering position.

38. The safety needle assembly according to claim 37, wherein a portion of the sheath contacts an interior surface of the protector when the sheath is in the initial position and when the protector is in the initial position to prevent the cannula engaging projection from lockingly engaging the cannula.

39. The safety needle assembly according to claim 34, wherein the protector includes an engaging part that engages a portion of the sheath as the protector is moved to separate the protector from the collar to cause the sheath to automatically pivot away from the initial position in a direction away from the cannula.

40. A safety needle assembly comprising:
a hub having a proximal end adapted to be connected to a fluid transfer device and a distal end;
a cannula having a proximal end connected to the hub and a distal end;
a collar mounted on the hub;
a protector positioned in an initial position in which the protector covers at least a portion of the cannula, the protector being movable from the initial position toward a removed position in which the cannula is uncovered by the protector, the protector having a wall provided with a through opening;
a sheath pivotally mounted on the collar in an initial position in which at least a portion of the sheath extends through the opening in the wall of the protector, the sheath including side walls and a back wall defining a channel, the sheath being adapted to be pivoted away from the cannula and out through the opening in the wall of the protector and being adapted to be pivoted back towards the cannula to a cannula covering position in which the cannula is positioned within the channel once the protector has been moved to the removed position; and
means for preventing the sheath in the initial position from freely pivoting out of the opening in the wall of the protector in the absence of a force causing pivoting movement of the sheath.

41. The safety needle assembly according to claim 40, wherein the means for preventing the sheath from freely pivoting out of the opening in the wall of the protector includes the opening in the wall of the protector having a width that is less than a distance between outer surfaces of the side walls of the sheath.

42. The safety needle assembly according to claim 41, wherein each of the side walls includes a tapered tip portion for facilitating passage of the side walls of the sheath through the opening in the wall of the protector.

43. The safety needle assembly according to claim 40, wherein the sheath includes a cannula retaining projection that lockingly engages the cannula to lock the sheath in the cannula covering position.

44. The safety needle assembly according to claim 43, wherein a portion of the sheath contacts an interior surface of the protector when the sheath is in the initial position to prevent the cannula engaging projection from lockingly engaging the cannula.

45. The safety needle assembly according to claim 40, wherein the protector includes an engaging part that engages a portion of the sheath during movement of the protector from the initial position toward the removed position to cause the sheath to automatically pivot away from the initial position.

* * * * *